United States Patent
Alonso Fernandez et al.

(10) Patent No.: US 10,471,020 B2
(45) Date of Patent: Nov. 12, 2019

(54) NANOPARTICLES WITH PROTECTED INTERIORS, AND METHODS OF USE THEREOF

(71) Applicant: Universidade de Santiago de Compostela, Santiago de Compostela (ES)

(72) Inventors: Maria Josefa Alonso Fernandez, Santiago de Compostela (ES); Zhigao Niu, Santiago de Compostela (ES); Manuel Jesus Santander Ortega, Albacete (ES)

(73) Assignee: Universidade de Santiago de Compostela, Santiago de Compostela (ES)

( * ) Notice: Subject to any disclaimer, the term of this patent is extended or adjusted under 35 U.S.C. 154(b) by 0 days.

(21) Appl. No.: 15/350,653

(22) Filed: Nov. 14, 2016

(65) Prior Publication Data

US 2018/0078510 A1    Mar. 22, 2018

(30) Foreign Application Priority Data

Sep. 19, 2016 (ES) .................................. 201631221

(51) Int. Cl.
*A61K 9/51* (2006.01)
*A61K 31/7088* (2006.01)
*A61K 38/28* (2006.01)

(52) U.S. Cl.
CPC .......... *A61K 9/5153* (2013.01); *A61K 9/5146* (2013.01); *A61K 31/7088* (2013.01); *A61K 38/28* (2013.01)

(58) Field of Classification Search
CPC ............................. A61K 38/28; A61K 9/5153
See application file for complete search history.

(56) References Cited

U.S. PATENT DOCUMENTS

| 8,709,472 B1 | 4/2014 | Murase et al. |
| 2015/0202322 A1 | 7/2015 | Sinko et al. |

FOREIGN PATENT DOCUMENTS

| CN | 104434806 A | 3/2015 |
| CN | 104497147 A | 4/2015 |
| EP | 2664324 A1 | 11/2013 |
| EP | 1676588 B1 | 12/2013 |
| EP | 2886128 A1 | 6/2015 |
| WO | 2018/050942 A1 | 3/2018 |

OTHER PUBLICATIONS

Herrero et al., Polymer-based oral peptide nanomedicines. Ther Deliv. May 2012;3(5):657-68.
Khafagy et al., Cell-penetrating Peptide-biodrug Strategy for Oral and Nasal Delivery: Review of Recent Findings. J Exp Clin Med. Aug. 2012;4(4):198-202.
Liang et al., Tumor-specific penetrating peptides-functionalized hyaluronic acid-d-α-tocopheryl succinate based nanoparticles for multi-task delivery to invasive cancers. Biomaterials. Dec. 2015;71:11-23. doi: 10.1016/j.biomaterials.2015.08.035. Epub Aug. 20, 2015.
Liu et al., Oligoarginine-modified biodegradable nanoparticles improve the intestinal absorption of insulin. Int J Pharm. May 1, 2013;448(1):159-67. doi: 10.1016/j.ijpharm.2013.03.033. Epub Mar. 25, 2013.
Tsiourvas et al., Insulin complexes with PEGylated basic oligopeptides. J Colloid Interface Sci. Oct. 15, 2012;384(1):61-72. doi: 10.1016/j.jcis.2012.06.068. Epub Jul. 4, 2012.
International Search Report and Written Opinion for Application No. PCT/ES2017/070617 dated Dec. 5, 2017.
Svilenov et al., Chapter 8: Solid Lipid Nanoparticles—A Promising Drug Delivery System. Nanomedicine. Faculty of Chemistry and Pharmacy, Sofia University, Bulgaria. 187-237.
Zhang et al., Solid lipid nanoparticles modified with stearic acid-octaarginine for oral administration of insulin. Int J Nanomedicine. 2012;7:3333-9. doi: 10.2147/IJN.S31711. Epub Jul. 2, 2012.
International Preliminary Report on Patentability for Application No. PCT/ES2017/070617 dated Mar. 28, 2019.

*Primary Examiner* — Kaipeen E Yang
(74) *Attorney, Agent, or Firm* — Wolf, Greenfield & Sacks, P.C.

(57) ABSTRACT

The present invention generally relates to particles, including nanoparticles, for example, for drug delivery or other applications. Certain aspects of the present invention are generally directed to particles, such as nanoparticles, comprising an inner portion and a coating. The inner portion may contain insulin or other therapeutic molecules for delivery to a living organism. In some cases, the molecules may be electrostatically complexed with an oppositely-charged peptide, such as an oligoarginine, or other species. The therapeutic molecules may also be water soluble. In some cases, the peptide may be conjugated to a hydrophobic portion, such as cholesterol, lauric acid, or a fatty acid chain. This hydrophobic modification may facilitate complex formation with the therapeutic molecule and the stability of the resulting complex. The complex typically is surrounded by a coating, which may protect the complex. For example, the coating may include polymers such as poly(glutamic acid) and poly(ethylene glycol). In some cases, the coated complex may also facilitate transport across cells, e.g., within the gastrointestinal tract. Other aspects of the invention are generally directed to methods of making or using such compositions, kits including such compositions, or the like.

21 Claims, 7 Drawing Sheets

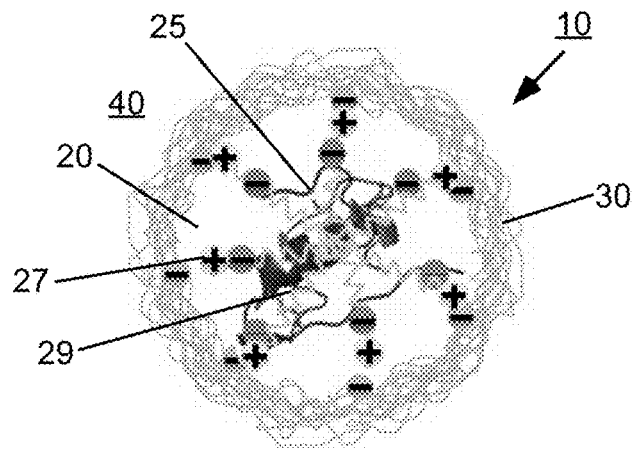
FIG. 12
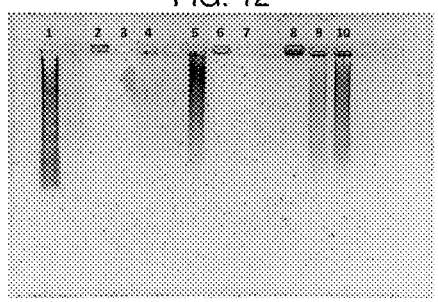
FIG. 13
FIG. 14A
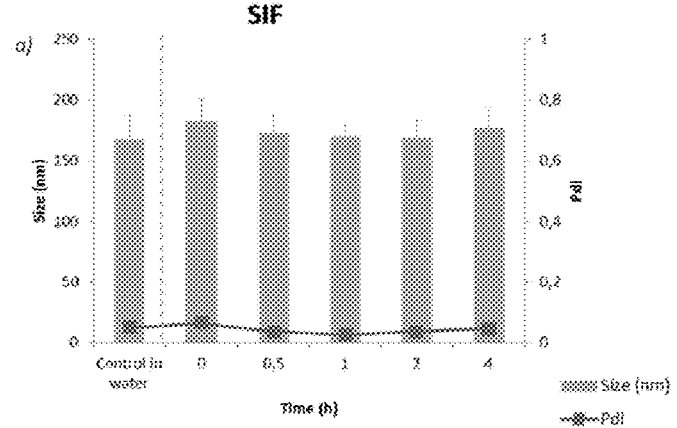
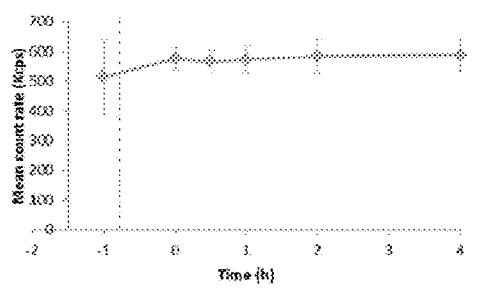
FIG. 14B

NANOPARTICLES WITH PROTECTED INTERIORS, AND METHODS OF USE THEREOF

RELATED APPLICATIONS

This application claims priority to Spanish Application Serial No. P201631221, filed 19 Sep. 2016, entitled "Nanoparticulas con Interiores Protegidos, y Metodos de Use de las Mismas," incorporated herein by reference in its entirety.

FIELD

The present invention generally relates to particles, including nanoparticles, for example, for drug delivery or other applications.

BACKGROUND

It is a huge challenge to deliver pharmaceutical agents into the body. For example, barriers associated with the oral modality of administration can prevent many pharmaceutical agents from being delivered orally. These barriers include pH and enzymes-mediated degradation throughout the gastrointestinal tract (GIT), and very limited transport across the intestinal mucosa. Accordingly, improvements in the delivery of pharmaceutical agents, e.g., orally, are still needed.

SUMMARY

The present invention generally relates to particles, including nanoparticles, for example, for drug delivery or other applications. The subject matter of the present invention involves, in some cases, interrelated products, alternative solutions to a particular problem, and/or a plurality of different uses of one or more systems and/or articles.

In one aspect, the present invention is generally directed to a composition. According to one set of embodiments, the composition includes a particle comprising an inner portion surrounded by a coating. In some cases, the inner portion comprises a complex of a negatively charged moiety, and a positively charged peptide comprising at least 3 arginine residues and linked to a hydrophobic portion. In certain instances, the coating comprises a polyacid and/or a polyalcohol.

In another set of embodiments, the composition comprises a nanoparticle comprising an inner portion surrounded by a coating, where the inner portion comprises a complex of insulin and a molecule comprising an octaarginine portion. In some embodiments, the coating comprises a copolymer of poly(glutamic acid) and poly(ethylene glycol).

The composition, in yet another set of embodiments, is directed to a particle comprising an inner portion surrounded by a coating. In some cases, the inner portion comprises a complex of a negatively charged peptide and a molecule comprising an octaarginine portion linked to a hydrophobic portion. In certain embodiments, the coating comprises poly(glutamic acid) and poly(ethylene glycol).

In still another set of embodiments, the composition comprises a particle comprising an inner portion surrounded by a coating. In some embodiments, the inner portion comprises a complex of a negatively charged peptide and a positively charged peptide comprising at least 3 arginine residues. In certain cases, the coating comprises poly(ethylene glycol).

Several methods are disclosed herein of administering a living organism with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In another aspect, the present invention encompasses methods of making one or more of the embodiments described herein, for example, a nanoparticle. In still another aspect, the present invention encompasses methods of using one or more of the embodiments described herein, for example, a nanoparticle.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 12 illustrates a particle according to yet another embodiment of the invention;

FIG. 13 illustrates an agarose gel assay showing association/dissociation of a polynucleotide from the complexes, in another embodiment of the invention;

FIGS. 14A-14B illustrate stability of certain complexes in still another embodiment of the invention.

DETAILED DESCRIPTION

Figure 1A:
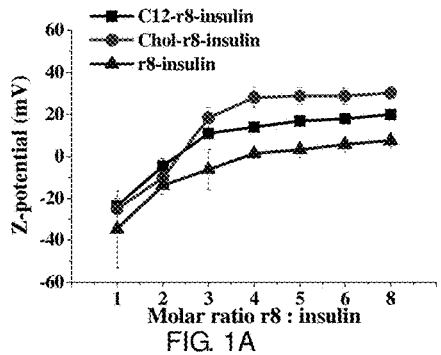
FIGS. 1A-1D illustrate certain properties of particles produced in various embodiments of the invention.
Figure 1B:
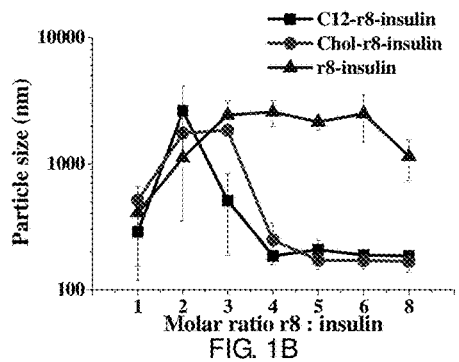

The present invention generally relates to particles, including nanoparticles, for example, for drug delivery or other applications. Certain aspects of the present invention are generally directed to particles, such as nanoparticles, comprising an inner portion and a coating. The inner portion may contain insulin or other therapeutic molecules for delivery to a living organism. In some cases, the molecules may be electrostatically complexed with an oppositely-charged peptide, such as an oligoarginine, or other species. The therapeutic molecules may also be water soluble. In some cases, the peptide may be conjugated to a hydrophobic portion, such as cholesterol, lauric acid, or a fatty acid chain. This hydrophobic modification may facilitate complex formation with the therapeutic molecule and the stability of the resulting complex. The complex typically is surrounded by a coating, which may protect the complex. For example, the coating may include polymers such as poly(glutamic acid) and poly(ethylene glycol). In some cases, the coated complex may also facilitate transport across cells, e.g., within the gastrointestinal tract. Other aspects of the invention are generally directed to methods of making or using such compositions, kits including such compositions, or the like.

One aspect of the present invention is now described with reference to FIG. 12. In this figure, particle 10 is shown. In some cases, particle 10 is a nanoparticle, e.g., having an average diameter of less than about 1 micrometer (e.g., less than about 200 nm, or other diameters as discussed herein). In this figure, particle 10 is idealized as being generally spherical, although in other embodiments, the particle may also be non-spherical.

Particle 10 includes an inner portion 20 and an outer portion or coating 30, which can evenly or unevenly surround inner portion 20. Coating 30 may protect inner portion 20, e.g., from the external environment. In some cases, coating 30 may serve to facilitate the targeting of particles 10 to a desired location, e.g., to certain cells within the gastrointestinal tract.

Inner portion 20 of particle 10 may contain insulin 25, and/or other suitable peptides or molecules, e.g., that are to be delivered to a living organism. It should be understood that insulin is used here by way of example and ease of presentation only; other suitable molecules for delivery are discussed in more detail below. Insulin 25, in this example, is complexed to an oppositely-charged species 27. For example, oppositely-charged species 27 can be a peptide, such as octaarginine (R8), that has multiple oppositely-charged amino acid residues that are able to interact electrostatically with insulin 25.

Species 27 may be hydrophobically modified. For instance, as shown in FIG. 12 is hydrophobic portion 29 which is covalently linked to species 27. For instance, hydrophobic portion 29 may be cholesterol, lauric acid, or a fatty acid chain; other examples are discussed in more detail below. Without wishing to be bound by any theory, it is believed that the combination of insulin 25, oppositely-charged species 27, and hydrophobic portion 29 serves to create a surprisingly stable complex held together by hydrophobic and/or electrostatic forces within inner portion 20. For instance, such hydrophobic portions may facilitate interaction of different hydrophobic portions of different species molecules with each other and/or with insulin 25, thereby promoting stability. In contrast, similar complexes lacking such hydrophobic portions typically result in larger, more heterogeneous complexes that vary and are more unstable, due to the lack of hydrophobic interactions that serve to stabilize the complex.

In FIG. 12, surrounding inner portion 20 is coating 30. In some cases, coating 30 may contain a polymer that protects the inner portion, e.g., against the external environment 40 surrounding particle 10. For instance, the external environment may be aqueous, or an acidic environment in some cases. In some embodiments, the coating may include biocompatible and/or biodegradable materials. In addition, in some cases, coating 30 may be selected to facilitate transport across cells, e.g., within the gastrointestinal tract, and/or coating 30 contain moieties that facilitate transport across cells. Examples of suitable coatings include, but are not limited to, polyacids and polyalcohols, such as poly(ethylene glycol), poly(glutamic acid), poly(lactic acid), as well as combinations of these and/or other materials or polymers. Further examples are discussed in more detail below.

The above discussion is a non-limiting example of one embodiment of the present invention generally directed to nanoparticles, for example, for oral delivery. However, other embodiments are also possible. Accordingly, more generally, various aspects of the invention are directed to various systems and methods for particles for oral delivery, or other applications.

For example, it should be understood that "particles," as used herein, are not necessarily perfectly spherical, nor must they be perfectly solid. In some cases, for instance, the particles may be composed of relatively softer or deformable materials, or even gels, liquids, etc. in some embodiments. The particles, in some embodiments, are nanoparticles, i.e., having an average diameter of less than about 1 micrometer. In some cases, however, the particles may be smaller, e.g., having an average diameter of less than about 800 nm, less than about 600 nm, less than about 500 nm, less than about 400 nm, less than about 300 nm, less than about 200 nm, or less than about 100 nm. The particle may be non-spherical; for example, the particle may be ellipsoid or irregularly shaped. The "average diameter" (or "characteristic diameter") of a non-spherical particle may be taken as the diameter of a perfect sphere having the same volume as the non-spherical particle.

In addition, in some embodiments, more than one particle or type of particle is present, and the particles may each independently have the same or different compositions, sizes, shapes, average diameters, etc. The average diameter of a plurality of particles may be taken as the numerical average of the average diameters of each of the particles, and the average diameter of the plurality of particles may include the diameters discussed above. Those of ordinary skill in the art will know of suitable techniques for determining particle sizes, e.g., using laser light scattering or microscopy techniques.

As noted, the particles may include an inner portion and a coating. The inner portion may be symmetrically or asymmetrically located within the particle. Sometimes, more than one inner portion may be present. The inner portion typically includes a peptide or other therapeutic molecule to be delivered. The insulin within the inner portion may be, for example, human insulin, recombinant insulin, pork insulin, or the like. In some cases, insulin analogs can be used instead of (or in addition to) insulin, such as insulin lispro, insulin asparat, insulin glulisine, insulin detemir, insulin degludec, insulin glargine, NPH insulin, etc. The peptide or other molecule may have any kind of activity, such as anti-pain, anti-obesity, anti-inflammatory, etc. Examples of other suitable molecules include, but are not limited to, proteins and peptides, such as GLP-1 analogs (e.g. exenatide, liraglutide, lixisenatide, albiglutide, dulaglutide, taspoglutide, semaglutide), GLP-2 analogs (e.g. teduglutide), somatropin, anakinra, dornase alpha, whey acidic proteins, SPARC or osteonectin proteins, Protein C, keratin subfamily A, human growth hormone or somatotropin, gonadotropin, angiopoietin, colony-stimulating factors (macrophage colony-stimulating factor, granulocyte colony-stimulating factor, granulocyte macrophage colony-stimulating factor), epidermal growth factor, erythropoietin, fibroblast growth factor, GDNF family of ligands, growth differentiation factor-9, hepatocyte growth factor, hepatoma-derived growth factor, insulin-like growth factors, keratinocyte growth factor, migration-stimulating factor, macrophage-stimulating protein, neurotrophins, placental growth factor, platelet-derived growth factor, thrombopoietin, transforming growth factors, vascular endothelial growth factor, chemokines, interferons (e.g. interferon alpha IIb, interferon alfacon-1, interferon alpha-n3, etc.), interleukins, lymphokines, tumour necrosis factors (e.g. tumor necrosis factor-alpha), Fc fusion proteins, contulakin-G peptides and derivatives, antiflammins, opioid peptides, lipopeptides (e.g. surotomycin), antigens, such as tetanus and diphtheria toxoids, hepatitis B, and monoclonal antibodies, such as elotuzumab, panitumumab, anti-TNF alpha antibodies, etc.

In some embodiments, the molecule to be delivered includes a charged molecule (e.g., having a predominant negative charge at a pH of 7). These molecules can be complexed with an oppositely-charged species. Such complexes are often held together or stabilized via non-covalent interactions between molecules, such as charge interactions, van der Waals forces, hydrophobic effects, or the like. For example, insulin, which is negatively charged at neutral pH, can electrostatically interact with positively charged species. In addition, insulin and/or other therapeutic molecules may interact with the hydrophobic region linked to the oppositely-charged species, when the complexation occurs at a pH close to the isoelectric point of the insulin or other molecule, e.g., when there is an equilibrium of positive and negative charges and its solubility decreases. Thus, in some embodiments, the inner portion may include a positively-charged species complexed with the insulin (or other molecule). A positively-charged species may include a peptide having one or more positively-charged residues, such as arginine, lysine, or histidine. The formal charges of a molecule may be determined at neutral pH.

As a non-limiting example, in one set of embodiments, insulin complexes with an oppositely-charged peptide comprising 3, 4, 5, 6, 7, 8, 9, 10, 11, 12, or more arginine residues. In some cases, the peptide may be a homoarginine peptide, i.e., containing only arginine residues, although in other cases, the peptide may also include other residues as well. In some embodiments, the peptide has between 3 and 12, or between 6 and 10 residues. Non-limiting examples of suitable peptides include triarginine ($R_3$ or RRR), hexaarginine ($R_6$ or RRRRRR), octaarginine ($R_8$ or RRRRRRRR), or decaarginine ($R_{10}$ or RRRRRRRRRR). As discussed above, these peptides are by way of example only; other positively-charged peptides include, but are not limited to, homolysine peptides (e.g., $K_6$, $K_8$, $K_{10}$, etc.), homohistidine peptides (e.g., $H_6$, $H_8$, $H_{10}$, etc.), peptides comprising one or more of arginine, lysine, or histidine, and the like. It should also be noted that for peptides such as these, the residues within the peptides may all be D-isomers, L-isomers, or any suitable combination of D- and L-isomers. Where no isomer is specified in a peptide, it should be understood that any isomer may independently be present for each residue in various embodiments, and that in one embodiment, all of the isomers that are present are the naturally-occurring (L-) isomers.

In some cases, the peptide may be relatively lysine-rich (e.g., at least 10% of the amino acid residues are lysine), such as transportan, MPG, Pep-1, or the like. In some cases, the peptide may be relatively arginine-rich (e.g., at least 10% of the amino acid residues are arginine), such as TAT (47-57) YGRKKRRQRRR; HIV-1 Tat-(48-60) GRKKRRQR-RRPPQ; Penetratin RQIKIYFQNRRMKWKK, and derivatives such as PenArg, Penlys; VP22 (267-301) DAATATRGRSAASRPTERPRAPARSASRPRRPVE; flock house virus (FHV) coating (35-49) RRRRNRTRRN-RRRVR; histidine-rich nona-arginine (HR9) C-5H-R9-5H-C; pas nona-arginine (PR9) FFLIPKG-R9; CADY* peptides Ac-GLWRALWRLLRSLWRLLWRA-cysteamide; or the like.

It should be understood, however, that the invention is not limited to only charged peptides. Other charged molecules can also be used in some embodiments of the invention, e.g., in addition to and/or instead of charged peptides. For example, in one set of embodiments, a negatively-charged polynucleotide may be used. Examples of such polynucleotides include, but are not limited to, homopolymers of nucleotides (e.g., polyadenosine, polyguanosine, polycytidine, or polythymidine, etc.), or polynucleotides comprising more than one base. Other non-limiting examples of suitable polynucleotides include DNA, antisense, splice-switching oligonucleotides, siRNA, miRNA, aptamers, immunostimulatory oligonucleotides, dsRNA, etc. The polynucleotides may be of any suitable length in various embodiments, e.g., at least 3, at least 5, at least 10, at least 30, at least 50, at least 100, at least 500, or at least 1000 nucleotides. The polynucleotides may include only naturally-occurring nucleotides, or in some cases, the polynucleotides may include non-naturally-occurring nucleotides. For instance, in one example, the polynucleotide may include poly (I:C), which is a mismatched double-stranded RNA with one strand being a polymer of inosinic acid, the other a polymer of cytidylic acid.

In addition, in certain embodiments, the species may include a hydrophobic moiety. For example, the species may be a peptide linked to a suitable hydrophobic moiety. Without wishing to be bound by any theory, it is believed that the hydrophobic portion may promote formation and stability of complexes. For instance, due to their hydrophobic nature, various hydrophobic portions of different molecules may interact with each other within the inner portion, which may promote stabilization of the complex. In some cases, insulin or other molecules to be delivered can also contain one or more hydrophobic regions, which can interact with such hydrophobic portions, thereby also promoting stability. In some cases, the hydrophobic portions may be portions that substantially separate from water when in isolated form.

Non-limiting examples of hydrophobic portions include sterols such as cholesterol, or fatty acids such as lauric acid (n-dodecanoic acid, $C_{12}$). In some embodiments, the hydrophobic portion may be linked, for example, covalently, to the oppositely-charged species and/or to the molecule to be delivered. For example, if the species is a peptide, such as triarginine, hexaarginine, octaarginine or other peptides discussed herein, a hydrophobic portion may be covalently linked to the C-terminus end and/or the N-terminus end of the peptide. The species may also be a polynucleotide, or other charged molecules such as those discussed herein.

Examples of sterols that can be used, in addition to (or instead of) cholesterol include, but are not limited to, lanosterol, dihydrolanosetrol desmosterol, dihydrocholesterol, stigmasterol, sitosterol, campesterol, brassicasterol, zymosterol, ergosterol, or the like. Other fatty acids that can be used in certain embodiments include, but are not limited to, branched or unbranched fatty acids, or saturated or unsaturated fatty acids, such as n-decanoic acid, n-undecanoic acid, n-tridecanoic acid, or n-tetradecanoic acid. Additional non-limiting examples of suitable unsaturated fatty acids include myristoleic acid, palmitoleic acid, sapienic acid, oleic acid, elaidic acid, vaccenic acid, linoleic acid, linoelaidic acid, alpha-linolenic acid (ALA), arachidonic acid, eicosapentaenoic acid, erucic acid, docosahexaenoic acid, etc. Additional non-limiting examples of suitable saturated fatty acids include caprylic acid, capric acid, lauric acid, myristic acid, palmitic acid, stearic acid, arachidic acid, behenic acid, lignoceric acid, cerotic acid, or the like. Still other examples of fatty acids include short-chain fatty acids (e.g., less than 10, 9, 8, 7, 6, 5, 4, or 3 carbons in the fatty acid portion) such as butyric and isobutyric acids, valeric and isovaleric acids, or the like. Those of ordinary skill in the art will be aware of techniques for attaching or linking a suitable hydrophobic portion to an oppositely-charged species and/or to a molecule to be delivered. For instance, coupling reactions or FMOC protection reactions can be used in some embodiments to link the hydrophobic portion to the oppositely-charged peptide.

Additional non-limiting examples of hydrophobic portions include cycloalkanes (e.g., cyclopropane, cyclobutane, cyclopentane, cylcohexane, etc.), bile salts, terpenoids, terpenes, terpene-derived moieties, and lipophilic vitamins such as vitamins A, D, E, K, and derivatives thereof. Non-limiting examples of bile salts include non-derivatized bile salts such as cholate, deoxycholate, chenodeoxycholate, and ursodeoxycholate, etc. Non-limiting examples of derivatized bile salts include taurocholate, taurodeoxycholate, tauroursodeoxycholate, taurochenodeoxycholate, glycholate, glycodeoxycholate, glycoursodeoxycholate, glycochenodeoxycholate, taurolithocholate, and glycolithocholate, etc.

The inner portion is typically surrounded by a coating, which may evenly or unevenly surround the inner portion of the particle. In some cases, the coating is substantially free of the materials forming the inner portion, e.g., charged species such as the peptide or other molecule to be delivered (e.g., insulin) and/or an oppositely-charged species (e.g., $R_8$ or other peptides as discussed above). For instance, less than 80%, less than 85%, less than 90%, less than 95%, less than 97%, or less than 99% of the inner portion materials (by mass) may be present in the coating of the particle. The coating may be formed simultaneously with the inner portion, or in certain embodiments, the coating may be added after formation of the inner portion (or complexes forming the inner portion).

In some embodiments, the coating includes one or more polymers, and the polymers may be biocompatible and/or biodegradable in some instances, e.g., the polymer may dissociate or degrade upon exposure to water (e.g., having a time constant of degradation of less than 1 or 2 years). The polymers may, for example, protect the inner portion against exposure or degradation, e.g., to the environment external to the particle. For example, the coating may protect the inner portion from exposure to oxygen, water, or acid in the external environment. As a non-limiting example, the particles may be contained in an environment having a pH of less than about 7.4, less than about 7, less than about 6, less than about 5, less than about 4, less than about 3, or less than about 2. Examples of suitable polymers for the coating include, but are not limited to, polyalcohols such as poly (ethylene glycol), poly(propylene glycol), poly(vinyl alcohol), polyacids such as poly(glutamic acid), poly(lactic acid), hyaluronic acid, etc., and alginate, as well as combinations of these and/or other materials or polymers. For example, the polymer may be a copolymer of any of these and/or other polymers, e.g., a copolymer of poly(ethylene glycol) and poly(propylene glycol). In some cases, polymers having a range of compositions and/or molecular weights may be used. Additional examples of polyalcohols include, but are not limited to, poly(vinyl alcohol), poly(vinylpyrrolidone), manitol, sorbitol, glycerol, polysorbates, sorbitane esters, poloxamers, or the like.

In addition, in certain cases, the coating may be selected to facilitate targeting of the particles, e.g., to a suitable target. For example, in one set of embodiments, the coating may facilitate transport into or across cells, e.g., within the gastrointestinal tract. In some cases, the particles may include targeting moieties, such as antibodies, to facilitate transport into or across a cell.

As another example, the coating may include a polymer of poly(glutamic acid) and/or poly(ethylene glycol), which may enhance stability of the particles, e.g., in biological fluids, and/or facilitate the diffusion of particles, e.g., across mucosal surfaces. Non-limiting examples of polymers of poly(glutamic acid) and/or poly(ethylene glycol) include those disclosed in Ep. Pat. Apl. Pub. No. EP 2 664 324, incorporated herein by reference in its entirety. In some cases, the poly(glutamic acid) (PGA) may include water soluble salts of PGA, such as the ammonium salt of PGA, or metal salts such as the lithium salt, sodium salt, potassium salt, magnesium salt, etc.

In one embodiment, the PGA form may include one or more of poly-D-glutamic acid, poly-L-glutamic acid, poly-D, L-glutamic acid, poly-alpha-glutamic acid, poly-alpha-D-glutamic acid, poly-alpha-L-glutamic acid, poly-alpha-D, L-glutamic acid, poly-gamma-glutamic acid, poly-gamma-D-glutamic poly-gamma-L-glutamic acid and poly-gamma-D,L-glutamic acid, and mixtures thereof. For example, the PGA may be poly-L-glutamic acid, the sodium salt of poly-L-glutamic acid, poly-alpha-glutamic acid, and/or the sodium salt of poly-alpha-glutamic acid.

In some cases, the coating includes poly(ethylene glycol) ("PEG"), e.g., separately, and/or incorporated with poly (glutamic acid), for example, in a copolymer, e.g., a branched or diblock copolymer. Poly(ethylene glycol), in its most common form, is a polymer of formula (I):

$$H-(O-CH_2-CH_2)_p-OH \qquad (I),$$

where p is an integer representing the PEG polymerization degree. For example, p may be less than about 1000, less than about 700, less than about 500, less than about 300, less than about 100, less than about 70, less than about 50, less than about 30, less than about 10, less than about 7, less than about 5, or less than about 3. In some cases, PEG may provide greater stability and/or an increased residence time, facilitating arrival at a target, e.g., cells within the gastrointestinal tract.

In certain embodiments, a modified PEG in which one or both terminal hydroxyl groups are modified is used to link the PEG to poly(glutamic acid). These include, but are not limited to, those of formula (II):

$$X^1-(O-CH_2-CH_2)_p-X^2 \qquad (II),$$

where $X^1$ is hydrogen or a hydroxyl protecting group blocking the OH function for subsequent reactions. p may be any number, e.g., as discussed above. The protective groups of hydroxyl radicals are known to those of ordinary skill in the art; non-limiting example representative protecting groups (already including the oxygen to be protected) are silyl ethers such as trimethylsilyl ether, triethylsilyl ether, tertbutyldimethylsilyl ether, tert-butyldiphenylsilyl ether, triisopropylsilyl ether dietilsopropilsilil ether texildimetilsilyl ether, triphenylsilyl ether, di-tert-butylmethylsilyl ether, alkyl ethers such as methyl ether, tert-butyl ether, benzyl ether, p-methoxybenzyl ether, 3,4-dimethoxybenzyl ether, trityl ether, allyl ether; alkoxymethyl ethers such as methoxymethyl ether, 2-methoxyethoxymethyl, benzyloxymethyl ether, p-methoxybencyloxymethyl ether, 2-(trimethylsilyl) ethoxymethyl ether, tetrahydropyranyl ether and related ethers; methylthiomethyl ether, esters such as acetate ester, benzoate ester, ester pivalate ester, methoxyacetate, chloroacetate ester, levulinate ester, carbonates such as benzyl carbonate, p-nitrobenzyl carbonate, tert-butyl carbonate, 2,2,2-trichloroethyl carbonate, 2-(trimethylsilyl) ethyl, allyl carbonate. In one embodiment, the protecting group is an alkyl ether, such as a methyl ether. $X^2$ may be a bridge group allowing the anchoring to polyglutamic acid groups and to groups of the derivatives thereof. In some cases, $X^1$ may be a group allowing the anchoring with other PGA and derivatives thereof.

In certain embodiments, the PEGs are attached to PGA and/or derivatives thereof via amine groups and/or carboxylic acid of the latter. PEGylation of the polymers can be performed using any suitable method available in the art.

In one set of embodiments, the polymer of the coating may include water-soluble derivatives of PGA or PGA-PEG, where PGA is substituted at one or more available positions, for example, amine groups and/or carboxylic acid, with one or more appropriate groups. Suitable derivatives of PGA and PGA-PEG derivatives include, but are not limited to, poly (alkylglutamine) and derivatives of PEG-poly(alkylglutamine) such as poly(N-2-(2'-hydroxyethoxy)ethyl-L-glutamine) (PEEG), PEG-PEEG, poly(N-3-(hydroxypropyl)-L-glutamine) (PHPG), PEG-PHPG, poly(N-2-(hydroxyethyl)-L-glutamine) (PHEG) PEG-PHEG, poly(gamma-benzyl-L-glutamate) (pBG), PEG-pBG, poly(gamma-trichloroethyl-L-glutamate) (pTCEG), pTCEG-PEG, poly (dimethylaminoethyl-L-glutamine) (pDMAEG), PEGp-DMAEG, poly(pyridinoethyl-L-glutamine) (pPyAEG), PEG-pPyAEG, poly(aminoethyl-L-glutamine) (pAEG), PEG-pAEG, poly(histamine-L-glutamine) (pHisG), PEG-pHisG, poly(agmatine-L-glutamine) (pAgmG), PEG-pAgmG, PEG stearate, and/or mixtures thereof.

Polymers such as any of those discussed above are available in a variety of molecular weights. Thus, as a non-limiting example, a suitable molecular weight (weight average) of PGA in PGA and PGA-PEG polymer may be between about 1 kDa and about 100 kDa, between about 5 kDa and about 80 kDa, between about 10 kDa and about 50 kDa, e.g., about 10 kDa, about 15 kDa, about 20 kDa, about 25 kDa, about 30 kDa or about 35 kDa, etc. In addition, it should be understood that the PGA that is present may have a single molecule weight, or a range of molecular weights.

A molecular weight PEG in PGA-PEG polymers and water soluble derivatives thereof can be between about 1 kDa and about 50 kDa, between about 2 kDa and about 40 kDa, between about 3 kDa to about 30 kDa, and about 4 kDa; as non-limiting examples, the PEG may have a molecular weight of about 5 kDa, about 6 kDa, about 7 kDa, about 8 kDa, about 10 kDa, about 15 kDa, about 20 kDa, about 21 kDa, about 22 kDa, about 23 kDa, about 24 kDa, about 25 kDa and about 30 kDa. In addition, it should be understood that the PEG that is present may have a single molecule weight, or a range of molecular weights.

In some cases, PGA-PEG polymers and water soluble derivatives thereof are available in a variety of degrees of PEGylation. This PEGylation degree is defined as the percentage of functional groups or functional groups PGA or PGA derivatives that are functionalized with PEG. Suitable PEGylation grades in PGA-PEG polymers and water-soluble derivatives thereof can be between about 0.1% and about 10%, about 0.2% and about 5%, between about 0.5% and about 2%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%, etc.

In some cases, the proportion of PEG in the PEG-PGA polymers and water-soluble derivatives thereof can be between about 10% and 90% (w/w) with respect to the total weight of the polymer, e.g., between about 15% and 80%, between about 20% and 70%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, or about 60%. As noted above, the PEG may have a single molecule weight, or a range of molecular weights.

In some embodiments, the coating may be functionalized with a targeting ligand. Examples include, but are not limited to, peptides, proteins, antibodies and antibodies fragments, aptamers, or the like.

In addition, in some embodiments, the environment may include one or more carbohydrates to facilitate lyophilization or preservation of the particles, e.g., in a dry state. Examples of suitable carbohydrates include, but are not limited to, trehalose or sucrose.

Another aspect provides a method of administering any composition discussed herein to a living organism. When administered, the compositions of the invention are applied in a therapeutically effective, pharmaceutically acceptable amount as a pharmaceutically acceptable formulation. As used herein, the term "pharmaceutically acceptable" is given its ordinary meaning. Pharmaceutically acceptable compositions are generally compatible with other materials of the formulation and are not generally deleterious to the living organism. Any of the compositions of the present invention may be administered to the living organism in a therapeutically effective dose. A "therapeutically effective" or an "effective" as used herein means that amount necessary to delay the onset of, inhibit the progression of, halt altogether the onset or progression of, diagnose a particular condition being treated, or otherwise achieve a medically desirable result. The terms "treat," "treated," "treating," and the like, generally refer to administration of the inventive compositions to a living organism. When administered to a living organism, effective amounts will depend on the particular condition being treated and the desired outcome. A therapeutically effective dose may be determined by those of ordinary skill in the art, for instance, employing factors such as those further described below and using no more than routine experimentation. For example, in one embodiment, the compositions are used herein to treat diabetes, e.g., through administration of insulin to the living organism, e.g., orally.

Some embodiments of the invention are generally directed to the use of a composition as disclosed herein for the preparation of a medicament. For instance, certain embodiments refer to the compositions disclosed herein for use in the treatment of diabetes.

In administering the compositions of the invention to a living organism, dosing amounts, dosing schedules, routes of administration, and the like may be selected so as to affect known activities of these compositions. Dosages may be estimated based on the results of experimental models, optionally in combination with the results of assays of compositions of the present invention. Dosage may be adjusted appropriately to achieve desired drug levels, local or systemic, depending upon the mode of administration. The doses may be given in one or several administrations per day.

The dose of the composition to the living organism may be such that a therapeutically effective amount of the composition reaches the active site of the composition within the living organism. The dosage may be given in some cases at the maximum amount while avoiding or minimizing any potentially detrimental side effects within the living organism. The dosage of the composition that is actually administered is dependent upon factors such as the final concentration desired at the active site, the method of administration to the living organism, the efficacy of the composition, the longevity of the composition within the living organism, the timing of administration, the effect of concurrent treatments (e.g., as in a cocktail), etc. The dose delivered may also depend on conditions associated with the living organism, and can vary from living organism to living organism in some cases. For example, the age, sex, weight, size, environment, physical conditions, or current state of health of the living organism may also influence the dose required and/or the concentration of the composition at the active site. Variations in dosing may occur between different individuals or even within the same individual on different days. In some cases, a maximum dose may be used, that is, the highest safe dose according to sound medical judgment. In some cases, the dosage form is such that it does not substantially deleteriously affect the living organism.

In certain embodiments, a composition of the invention is administered to a living organism who has diabetes, or to a living organism who has a genetic predisposition for diabetes. Administration of a composition of the invention may be accomplished by any medically acceptable method which allows the composition to reach its target. The particular mode selected will depend of course, upon factors such as those previously described, for example, the particular composition, the severity of the state of the living organism being treated, the dosage required for therapeutic efficacy, etc. As used herein, a "medically acceptable" mode of treatment is a mode able to produce effective levels of the composition within the living organism without causing clinically unacceptable adverse effects.

Any medically acceptable method may be used to administer the composition to the living organism. The administration may be localized (i.e., to a particular region, physiological system, tissue, organ, or cell type) or systemic, depending on the condition to be treated. For example, the composition may be administered orally, or through other techniques such as vaginally, rectally, buccally, pulmonary, topically, nasally, transdermally, through parenteral injection or implantation, via surgical administration, or any other method of administration where access to the target by the composition of the invention is achieved. Oral administration is used in some embodiments because of the convenience to the living organism as well as the dosing schedule. Compositions suitable for oral administration may be presented as discrete units such as hard or soft capsules, pills, cachettes, tablets, troches, or lozenges, each containing a predetermined amount of the active compound. Other oral compositions suitable for use with the invention include solutions or suspensions in aqueous or non-aqueous liquids such as a syrup, an elixir, or an emulsion. In another set of embodiments, the composition may be used to fortify a food or a beverage. Rectal administration can be used in some embodiments, for example, in the form of an enema, suppository, or foam.

In certain embodiments of the invention, the administration of a composition of the invention may be designed so as to result in sequential exposures to a composition over a certain time period, for example, hours, days, weeks, months, or years. This may be accomplished, for example, by repeated administrations of a composition of the invention by one of the methods described above. Administration of a composition can be alone, or in combination with other therapeutic agents and/or compositions.

In certain embodiments of the invention, a composition can be combined with a suitable pharmaceutically acceptable carrier, for example, as incorporated into a liposome, incorporated into a polymer release system, or suspended in a liquid, e.g., in a dissolved form or a colloidal form. In general, pharmaceutically acceptable carriers suitable for use in the invention are well-known to those of ordinary skill in the art. As used herein, a "pharmaceutically acceptable carrier" refers to a non-toxic material that does not significantly interfere with the effectiveness of the biological activity of the active compound(s) to be administered, but is used as a formulation ingredient, for example, to stabilize or protect the active compound(s) within the composition before use. The term "carrier" denotes an organic or inorganic ingredient, which may be natural or synthetic, with which one or more active compounds of the invention are combined to facilitate the application of a composition as discussed herein. The carrier may be co-mingled or otherwise mixed with one or more compositions of the present invention, and with each other, in a manner such that there is no interaction which would substantially impair the desired pharmaceutical efficacy. The carrier may be either soluble or insoluble, depending on the application. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble. Those skilled in the art will know of other suitable carriers, or will be able to ascertain such, using only routine experimentation.

In some embodiments, a composition of the invention can include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients include diluents such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. A composition as discussed herein can be formulated into preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and emulsions, which can be isotonic with the blood of the living organism in certain embodiments. Examples of nonaqueous solvents are polypropylene glycol, polyethylene glycol, vegetable oil such as olive oil, sesame oil, coconut oil, arachis oil, peanut oil, mineral oil, injectable organic esters such as ethyl oleate, or fixed oils including synthetic mono or di-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating a composition as discussed herein without resort to undue experimentation.

The present invention also provides any of the above-mentioned compositions in kits, optionally including instructions for use of the composition for the treatment of diabetes or other diseases. Instructions also may be provided for administering a composition by any suitable technique as previously described, for example, orally.

The invention also involves, in another aspect, promotion of the treatment of diabetes or other diseases according to any of the techniques and compositions and composition combinations described herein. In some embodiments, one or more compositions of the invention can be promoted for treatment of diabetes or includes instructions for treatment of diabetes as mentioned above. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of a disease. "Instructions" can define a component of promotion, and typically involve written instructions on or associated with packaging of compositions of the invention. Instructions also can include any oral or electronic instructions provided in any manner. The kit typically defines a package including any one or a combination of a composition of the invention and the instructions, which may be of any form that is provided in connection with the composition in a manner such that a clinical professional will clearly recognize that the instructions are to be associated with the specific composition.

The kits described herein may also contain one or more containers, which may contain the inventive composition and other ingredients as previously described. The kits also may contain instructions for mixing, diluting, and/or administrating a composition of the invention in some cases. The kits also can include other containers with one or more solvents, surfactants, preservative and/or diluents (e.g., normal saline (0.9% NaCl), or 5% dextrose) as well as containers for mixing, diluting or administering the composition in a sample or to a living organism in need of such treatment.

The compositions of the kit may be provided as any suitable form, for example, as liquid solutions or as dried powders. When a composition provided is a dry powder, the composition may be reconstituted by the addition of a suitable solvent, which may also be provided. In embodiments where liquid forms of a composition are used, the liquid form may be concentrated or ready to use. The solvent will depend on a composition and the mode of use or administration. Suitable solvents for drug compositions are well known, for example as previously described, and are available in the literature. The solvent may depend on the composition and the mode of use or administration.

The following examples are intended to illustrate certain embodiments of the present invention, but do not exemplify the full scope of the invention.

EXAMPLE 1

Figure 3A:
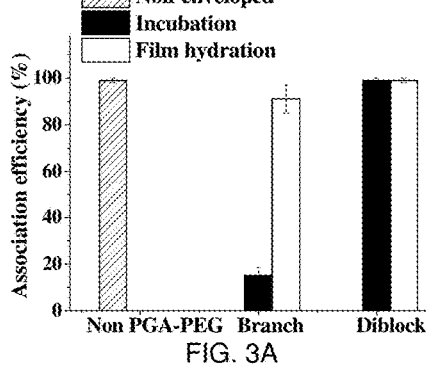
FIGS. 3A-3C illustrate peptide association, in some embodiments of the invention.
Figure 3B:
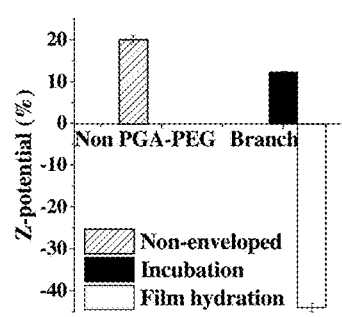
Figure 3C:
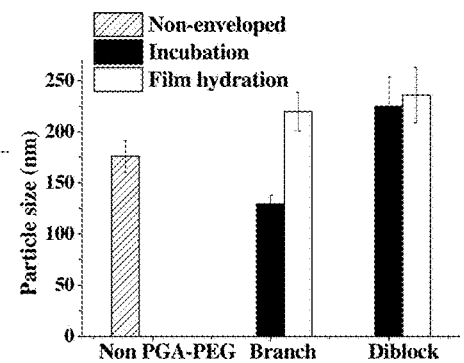
Figure 4:
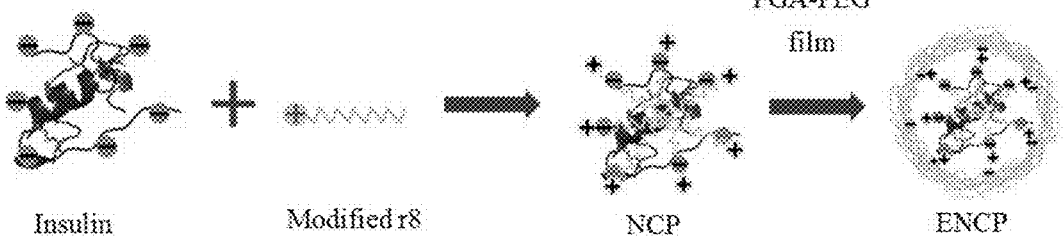
FIG. 4 illustrates preparation of a particle in one embodiment of the invention.
Figure 6A:
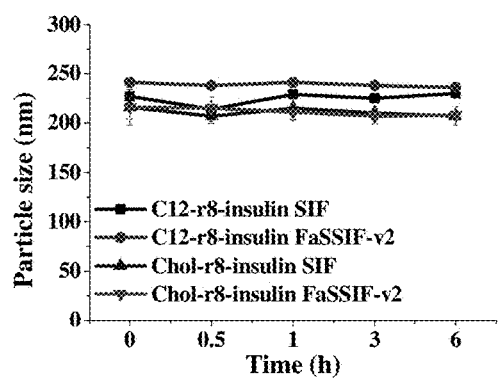
FIGS. 6A-6B illustrate colloidal stability, according to certain embodiments of the invention.
Figure 6B:
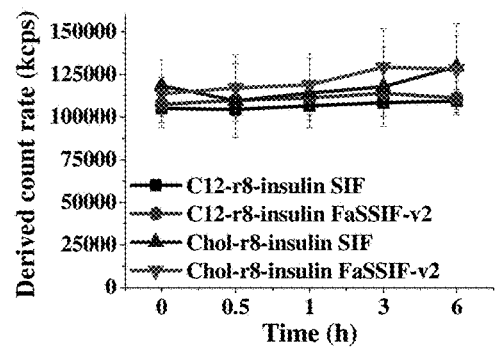
Figure 7:
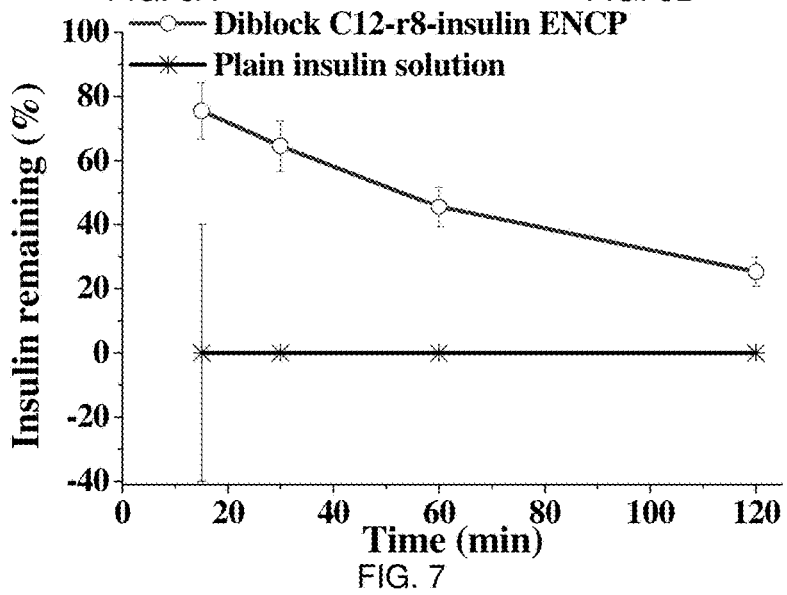
FIG. 7 illustrates stability against proteolysis, in another embodiment of the invention.
Figure 9A:
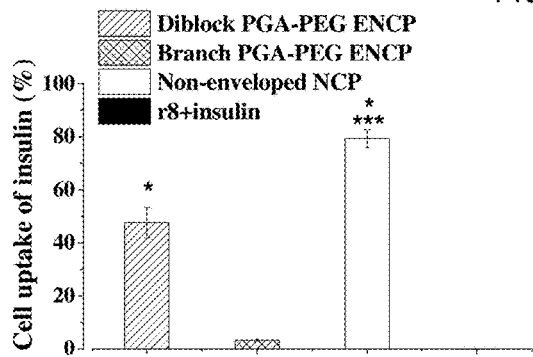
FIGS. 9A-9B illustrate insulin transport, in still other embodiments of the invention.
Figure 9B:
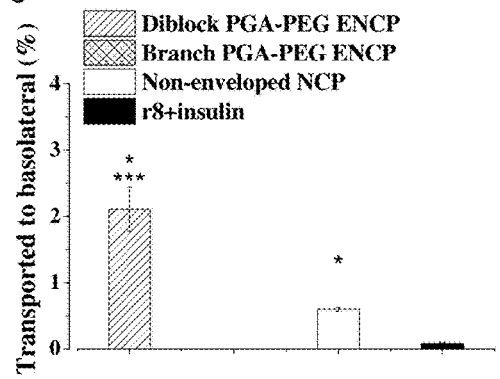

Cell penetrating peptides (CPPs), i.e., octaarginine (R8), may be useful as a way to enhance the transport of insulin across the intestinal epithelium. The following examples illustrate the design and engineering of an R8-based peptide nanocarrier endowed with the capacity to prevent insulin from degradation, and facilitate its transport across the intestinal epithelium. For this, R8 was chemically conjugated with cholesterol (Chol) or lauric acid (C12) to form polyelectrolyte nanocomplexes with insulin. These nanocomplexes (NCPs) were enveloped with poly(glutamic acid)-poly(ethylene glycol) (PGA-PEG) in order to preserve their stability in the intestinal medium and facilitate their diffusion across the intestinal mucus. The enveloped NCP of the polymer (PGA-PEG) is shown in FIG. 4 named ENCP. The enveloped C12-R8-insulin NCPs (ENCPs) with a hydrophilic polymer, for example PGA-PEG, exhibited an average particle size of 200 nm, a narrow size distribution (PdI 0.1), a negative (−44+/−1 mV) or neutral (+2+/−2 mV) zeta potential, and a 100% insulin association efficiency (AE) (FIGS. 3A-3C). The characteristics of these particles are very similar to those wherein the envelop is hyaluronic acid instead of PGA. However, this is in opposition with regular R8-insulin complexes in the absence of the envelope, whose size was variable and in the micrometer range. As expected from their design, ENCPs showed good colloidal stability and the capacity to effectively protect insulin from proteolysis in simulated intestinal fluids (SIF) with pancreatin (FIGS. 6A, 6B, and 7). In addition, studies performed in Caco-2 cells indicated that ENCPs led to 47.59% insulin cell uptake and 2.11% insulin transport to the basolateral side of the cell monolayer, whereas the physical mixture of R8 with insulin led to negligible insulin transport (FIGS. 9A and 9B). Finally, permeability studies across human intestine also showed that ENCPs were capable of penetrating the mucus layer that cover intestinal cells (FIG. 15, courtesy of Prof. Artursson and Prof. Lundsquik). Overall, these data showed that the combination of amphiphilic penetration enhancers derived of CPPs in combination with PEGylating protecting polymers may represent a useful strategy for making feasible the oral administration of peptides.

Figure 15A:
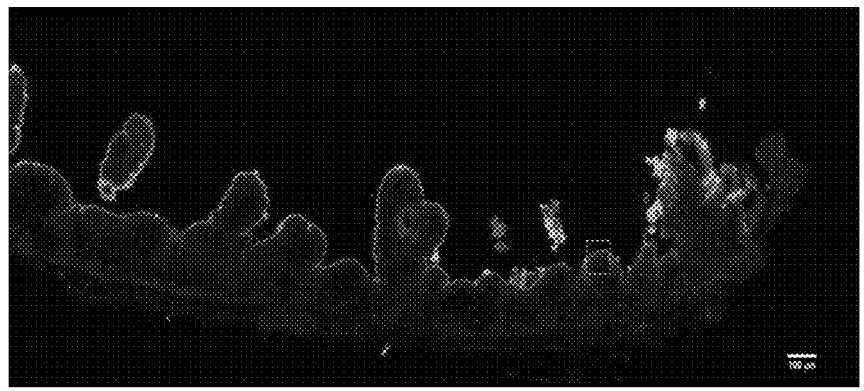
FIGS. 15A-15B illustrate the interaction of PGA-PEG coated R8-insulin nanocomplexes with the human intestinal epithelium, in another embodiment of the invention.
Figure 15B:
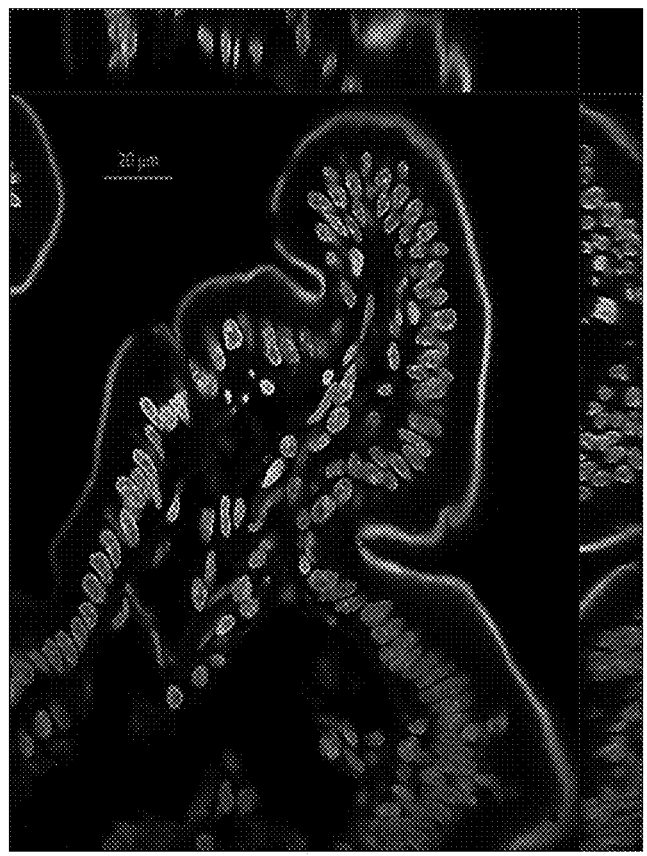

FIGS. 15A-15B illustrate the interaction of PGA-PEG coated R8-insulin nanocomplexes with the human intestinal epithelium (Cryosection; conventional LSM imaging, orthogonal view). The human tissue was mounted in a "Ussing" chamber and exposed to fluorescently labeled (FITC) insulin-loaded nanocomplexes. The nuclei of the cells were stained in blue.

Design of the insulin nanocarrier in these examples, in addition to R8, included additional elements for confronting the multiple biological barriers. First, in order to increase the stability of the insulin-CPP complex, specific R8 hydrophobic derivatives were used to tightly associate insulin not only by electrostatic interaction, but also with hydrophobic forces. Moreover, these stable nano-size complexes were further enveloped with a polymer that could prevent the attachment of intestinal enzymes, e.g., pancreatin, followed by the degradation of the entrapped insulin. For this, poly-glutamic acid-PEG (PGA-PEG) was used, taking into account that the acidic chain could interact with the cationic insulin-R8 complex, thereby projecting the PEG molecule towards the external phase. This PEG coating additionally facilitated the diffusion through intestinal mucus. In the present examples, the physicochemical characteristics and AE of the NCPs and ENCPs were determined; colloidal stability of in simulated intestinal media and under storage was evaluated; drug protection effect against proteolysis was checked; the in vitro release profile, cytotoxicity, cell uptake and transport studies on Caco-2 models were performed and the toxicity and permeability of the formulation was finally corrected or confirmed in human jejunal tissue.

Recombinant human insulin monomer insulin (Apidra®, Mw 5823 Da) was kindly provided by Sanofi (Paris, France). Fmoc-D-Arg(Pbf)-OH was purchased from Iris Biotech GmbH (Marktredwitz, Germany). Branch ([PGA]$_{100}$-m[PEG]$_6$ poly(L-glutamic acid gamma-(omega-methoxyhepta (ethylene glycol))) sodium salt, 10-20 mol % mPEG substitution, MW=22.8k-24.7 kDa, 14-27% PEG) was purchased from Polypeptide Therapeutic Solutions (PTS, Valencia, Spain). Diblock (m[PEG]$_{455}$-b-[PGA]$_{10}$, methoxy-poly(ethylene glycol)-block-poly(L-glutamic acid sodium salt), MW=22 kDa, 20 kDa PEG and 2 kDa PGA) was purchased from Alamanda Polymers (Huntsville, USA). Lauric acid, cholesteryl chloroformate, pancreatin (8×USP), monobasic potassium phosphate, maleic acid, sodium chloride, and sodium hydroxide were purchased from Sigma Aldrich (St. Louis, USA). Sodium taurocholate was purchased from New Zealand Pharmaceuticals (Palmerston North, New Zealand). Soy lecithin was purchased from Archer Daniels Midland (Chicaco, USA). Human colorectal adenocarcinoma Caco-2 cells (ATCC® HTB37™) were purchased from American Type Culture Collection (Manassas, Va., USA). High glucose Dulbecco's modified eagle medium (DMEM) and non-essential amino acid (NEAA) solution were purchased from Sigma Aldrich (St. Louis, USA), while heat inactivated fetal bovine serum (FBS), penicillin-streptomycin solution, L-glutamine, phosphate-buffered saline (PBS), Dulbecco's phosphate-buffered saline with calcium and magnesium (DPBS) were purchased from Lonza (Basel, Switzerland). Ultrapurified water was obtained from Millipore Milli-Q Plus water purification system (Darmstadt, Germany). All other chemicals were of analytical grade.

Synthesis of C12-R8 and Chol-R8. C12-R8 and Cholesterol-R8 were synthesized by solid-phase peptide synthesis (SPPS) following a Fmoc/tBu strategy. Fmoc-Rink amide ChemMatrix® resin was used for obtaining an amide group in the C-terminus of both peptides. N,N,N',N'-tetramethyl-O-(benzotriazol-1-yl)uranium (TBTU) and N,N-diisopropylethylamine (DIEA) were used as coupling reagents for every amino acid incorporation (all amino acids were in the D-form). Fmoc deprotection was performed by the addition of 20% piperidine in DMF. Lauric acid and cholesteryl chloroformate were coupled to the N-terminus using the same strategy. Complete cleavage of both peptides from the resin and removal of the side-chain protecting groups were achieved by using the following cleavage cocktail:TFA/H$_2$O/TIS (95%/2.5%/2.5%). In terms of the FITC labeled C12-R8, introduction of a D-lysine, orthogonally protected, to the C-terminal of the peptides allowed the incorporation of 5(6)-carboxyfluorescein (CF) to the peptide sequence. Once the peptide was synthesized, C12 was coupled to the N-terminal. Then, an Alloc protecting group was selectively removed from the D-lysine side chain by treatment with tetrakis(triphenylphosphine) palladium (0) followed by incorporation of CF using standard amino acid coupling conditions. Both peptides were then purified by RP-HPLC at semi-preparative scale and characterized by HPLC (Waters Alliance 2695, photodiode array detector 2998 Waters, Sunfire C$_{18}$ column (100×4.6 mm×3.5 micrometers, 1 mL/min Acetonitrile (0.036% TFA) and H$_2$O (0.045% TFA). 8-min linear gradients were used in all cases) and MALDI spectrometry (MALDI-TOF Applied Biosystem 4700). All the peptides were obtained with a purity higher than 90%.

Preparation of the non-coated NCPs. C12-R8-insulin and Chol-R8-insulin NCPs were made based on hydrophobic and ionic interactions. Briefly, C12-R8 or Chol-R8 were dissolved in water at the concentration of 1 mg/mL. Insulin was dissolved at concentration 1 mg/mL at several pH's to explore the influence of pH (charge) on complexation with modified R8, and finally, 0.01 N NaOH (pH~11.8) was selected. The complexes were formed instantly upon mixing the solutions under magnetic stirring at different R8:insulin ratios (1:1 to 8:1). Simultaneously, blank controls were prepared by adding 0.01 N NaOH solution to C12-R8 or Chol-R8 solution to confirm that, in the absence of insulin, there was no nanoparticle or micelle formation. Additionally, a solution of non-hydrophobized R8 was used instead of C12-R8 or Chol-R8 in order to form a complex insulin. The characteristics of this complex were compared with the C12-R8 or Chol-R8 based prototypes. The pH of all NCPs was finally adjusted to 7 with HCl after the completion of the complexing process.

Preparation of PGA-PEG enveloped NCPs (ENCPs). The NCPs that resulted from the complexation process had a positive charge, and were enveloped by negatively charged diblock or branch type PGA-PEGs with different PEG length, leading to the formation of ENCPs. A film hydration method for envelopment was adopted, as it led to a good envelopment of the NCP without compromising the AE of insulin. PGA-PEG polymers were dissolved in water at concentration 1 mg/mL and the water phase was evaporated in a round flask under reduced pressure at 37° C., leading to the formation of a thin film. Then, the NCPs were transferred to the same flask and maintained for 10 min under rotation. Upon enveloping of the NCPs with the film, the pH of the final ENCPs suspension was adjusted to 7 with HCl.

Physicochemical characterization. Particle size and PdI of both NCPs and ENCPs were determined by Dynamic Light Scattering (DLS) using Malvern Zeta-Sizer (NanoZS, ZEN 3600, Malvern Instruments, Worcestershire, UK) fitted with a red laser light beam (wavelength 632.8 nm). The Z-potential was calculated from the mean electrophoretic mobility values determined by Laser Doppler Anemometry (LDA) using the same device. For the measurement of size and PdI, 50 microliters of the formulations was transferred directly into a particle size cuvette without any dilution. In Z-potential measurements, 400 microliters of the sample was diluted with 400 microliters of 1 mM KCl solution. A minimum amount of three batches of each formulation was analyzed and each batch was analyzed in triplicate. The morphological analysis of the NCPs and ENCPs was carried out with transmission electron microscopy (TEM, CM12, Philips, Netherlands). The samples were stained with phosphotungstic acid (2%, w/v) solution and placed on cupper grids with Formvard® for TEM observation.

Association efficiency and loading of insulin. Insulin association efficiency (AE) to NCPs and ENCPs was determined by both indirect and direct methods, following separation of the insulin complexes from the aqueous media and measuring the free insulin in the suspension media or the insulin involved in the ENCPs. 300 microliters of formulation were isolated by centrifugation (Hettich, Universal 32R, Germany) at 15,000 g for 15 min at 15° C. For the indirect method, the aqueous supernatant was collected and the amount of free insulin was determined by reverse phase HPLC (Agilent, 1100 Series, USA) method, using a C18 column (Superspher® RP-18 endcapped) as stationary phase, and the buffer of phosphoric acid and sodium perchlorate mixed with acetonitrile at different volume ratio as mobile phases (93:7 as phase A and 43:57 as phase B). The AE of insulin in the formulation was calculated according to the equation:

$$AE\ (\%) = \frac{\text{Total insulin} - \text{Free insulin}}{\text{Total insulin}} \times 100,$$

where Total insulin is the theoretical total insulin amount involved in the formulation, and Free insulin is the insulin amount determined by HPLC.

For direct measurements, 200 microliters of 0.1N NaOH (pH~12.8) and 100 microliters of DMSO were added successively to the sediment containing the ENCPs at 3000 rpm using a Vortex (VELP Scientifica, Italy). The solution was injected into the HPLC system and the AE was calculated dividing the insulin amount determined in the ENCP sediment by the total insulin amount involved in the formulation.

The final loading was calculated dividing the amount of insulin associated (AE×total insulin in the formulation) by the theoretical amount of all the materials involved in the formulation.

Colloidal stability study in simulated intestinal media. The colloidal stability of the NCPs and ENCPs was assessed upon their incubation in simulated intestinal medium (SW, pH 6.8, British Pharmacopoeia) and also in fasting-state simulated intestinal fluid (FaSSIF-V2, pH 6.5) for up to 6 hours at 37° C. FaSSIF-V2 is an updated version of FaSSIF in pharmacopeia, to better mimic in vivo intestinal conditions, and the composition of standard SIF and FaSSIF-V2 media are shown in Table 1. For each study, 200 microliters of the nanoparticles suspensions were diluted in 200 microliters of the corresponding media (0.06%, w/v), and then placed in a 37° C. incubator (Heidolph Instruments GmbH & Co. KG, Schwabach, Germany) with a horizontal shaking of 300 rpm. At different times (0 h, 0.5 h, 1 h, 3 h, and 6 h), 50 microliter samples of the incubation milieu were withdrawn for the analysis of particle size, PdI and derived count rate (dCR) with Malvern Zeta-Sizer. The dCR was used as an indicator of the concentration of the tested particles. At least three batches of the different formulations were analyzed and each analysis was done in triplicate.

TABLE 1

| Composition | SIF | FaSSIF-V2 |
|---|---|---|
| Sodium hydroxide | 15.4 mM | 34.8 mM |
| Monobasic potassium phosphate | 50 mM | — |
| Sodium taurocholate | — | 3 mM |
| Lecithin | — | 0.2 mM |
| Maleic acid | — | 19.12 mM |
| Sodium chloride | — | 68.62 mM |
| pH | 6.8 | 6.5 |

Stability during storage. For the determination of the colloidal stability under storage the nanoparticles suspensions were stored at different temperatures: at 4° C., room temperature (about 20° C.) and 37° C. for up to 2 months. The measurements of the particle size, PdI and dCR were performed in the same way as described above.

Additionally, a lyophilization study of the ENCPs was performed to assess the possibility to process the nanoparticles suspension as a powder. For this sucrose or trehalose (2%, w/v) was added to the nanoparticles suspension (0.12%, w/v) prior to freeze-drying (~50 hours circle) in order to facilitate the posterior re-suspension. The stability of the freeze dried ENCPs stored at room temperature for 2 months in a desiccator was also analyzed, by measuring their particle size after reconstitution of the freeze-dried system. The measurements of size, PdI and dCR were done in the same way as described above.

In vitro release study. An in vitro release study of the NCPs (C12-R8-insulin and Chol-R8-insulin) and the corresponding ENCPs was carried out in both SIF and FaSSIF-V2 media. Briefly, insulin loaded ENCPs suspension was diluted in 10 mL of SIF or FaSSIF-V2 (insulin concentration 0.17 mg/mL and 0.05 mg/mL). Immediately after the dispersion of formulation in SIF or FaSSIF-V2, an aliquot of 500 microliters was withdrawn and centrifuged at 15,000 g and 15° C. for 15 min. The same volume was added to replenish the release medium. The supernatant was carefully collected to determine the concentration of released insulin by HPLC analysis. The insulin concentration at this point was considered the value of time 0 hours. The rest of the sample was placed in 37° C. incubator with 300 rpm horizontal shaking for 24 hours, and during this time, 500 microliter samples were taken at 0.5, 1, 2, 6 and 24 hours to determine the released insulin at each of these time points. The medium was replenished at each time point and the total insulin concentration was calculated taking into account the dilution of the samples for each time interval. A different study was performed using 100 mM pH 4.0 or 5.0 acetate buffer or pH 2.5 acidified water in order to understand whether the ionic interaction between insulin and C12-R8 is the dominant factor preventing the release of the insulin from ENCPs, the release study with the same method.

Proteolysis study. To detect the capacity of the ENCPs to protect insulin from enzymatic degradation, a proteolysis study was performed by incubating ENCPs in SIF containing 1% (w/v) pancreatin. A volume of 250 microliters of the diblock PGA-PEG enveloped C12-R8-insulin ENCPs were incubated with 250 microliters of the proteolysis medium at 37° C. under 300 rpm horizontal shaking. At different time points, the samples were transferred to cold tubes containing 300 microliters of 0.1 N HCl, in order to quench the enzymatic proteolysis and the insulin content was quantified by LC-MS (Shimadzu HPLC system LC 20AD, Thermo Triple quadrupole mass spectrometer Quantum Ultra). The study was done in 3 replicates (from three different batches of nanoparticles). Plain insulin solution instead of the ENCPs was treated with the same proteolysis medium as control group. To exclude the interference of the pancreatin in LC-MS analysis, the proteolysis medium alone was set as another control.

Culture of Caco-2 cells. Caco-2 cells were grown in DMEM high glucose with L-glutamine supplemented with 10% heat inactivated fetal bovine serum, 1% penicillin (100 U/mL), streptomycin (100 micrograms/mL), and 1% NEAA solution. Cells were maintained at 37° C. in a humidified incubator supplied with 5% $CO_2$/95% air atmosphere.

Cytotoxicity study on Caco-2 cells. Cytotoxicity was determined using a MTS assay as an indicator of cell viability. Cell viability was assessed after the co-incubation of 10,000 Caco-2 cells/well on a 96-well tissue cultured plate (Costar® Corning®) with the aforementioned formulations in dispersion in culture DMEM medium supplemented with 4 mM of glutamine, 100 U/mL of penicillin, 100 microgram/mL of streptomycin and 20 of heat inactivated fetal bovine serum. Microplates were transferred to a humidified incubator at 37° C. with 5% $CO_2$ for 2 h or 24 h. After 2 h or 24 h of incubation, the supernatant of each well was removed, and the cells were incubated with 100 microliters of 3-(4,5-dimethylthiazol-2-yl)-5-(3-carboxymethoxyphenyl)-2-(4-sulfophenyl)-2H-tetrazolium (MTS) reagent at 37° C. for 2 h and 30 min in a humidified, 5% $CO_2$ atmosphere. The EC50 value for the different formulations were calculated from the dataset by non-linear regression analysis using GraphPad Prism.

Measurement of the trans-epithelial electrical resistance (TEER). Caco-2 cell monolayers were cultured on the tissue-cultured-treated PET filter (diameter 1 micrometer, growth area 1.1 $cm^2$) in Millipore Transwell® 12 wells/plates and were used for transport experiments 21 days after seeding. Evaluation of R8 based ENCPs and C12-R8 was investigated in Caco-2 cell monolayers. The change of TEER for the tightness of cell monolayers was measured with a Millicell-Electrical Resistance System (Endohm-12, Millipore Corp). Monolayers with a TEER values in the range of 800-1500 Ohm·$cm^2$ were used. Simultaneously, samples were collected (500 microliters) from the receiver compartment and the apical compartment 2 h after ENCP or C12-R8 cell monolayer exposure and insulin concentrations were measured using LC/MS. The cell monolayer was washed extensively in 0.9% NaCl and frozen at −80° C. for insulin quantification within the cells.

Quantitative cell uptake and transport studies. Liquid chromatography (Shimadzu HPLC system LC 20AD) with a 150×2.1 mm-5 micrometer-300 Angstrom HPLC $C_8$ column (Interchim) was used for elution of insulin. The mobile phase was A/B, where solvent A was $H_2O$ containing 0.1% formic acid and solvent B was acetonitrile containing 0.1% formic acid; the flow rate was 0.6 mL/min to avoid a pressure rise. An aliquot (100 microliters) of the sample was treated with 200 microliters of choloform/methanol/water at a ratio of 1/1/0.3 and 100 microliters of 0.1M NaOH, and then 40 microliters of analyte was injected onto the column placed in an oven at 60° C. The total run time was 13 min. Detection was done by tandem mass spectrometry (Quantum Ultra) in positive electrospray mode. The limit of detection was 0.005 micrograms insulin. System control and data processing were carried out using MassLynx software version 4.1. The spray voltage was 3.0 kV, and sheath and auxiliary gas pressures were 50 and 15 (arbitrary units), respectively. The in-source CID energy was fixed at 12 V, and capillary temperature was 350° C. The tube lens and collision energy values were optimized for insulin. Multiple reaction monitoring was used for the detection of the ion transitions. The multiple reaction monitoring transitions for analytes were as follows: m/z Insulin 890.56>984.55, m/z bovine insulin 1284.73>1104.60. Analytes were quantified by means of calibration curves using bovine insulin as internal standard. The standard curves showed linearity for creatine over a range of 0.025 to 10 micrograms·$mL^{-1}$ for insulin. The methodology for this assay involves reduction with dithiolthreitol 45 mM and alkylation with 100 mM of iodoacetamide 100 mM of intact insulin for measurement of the free B chain.

Toxicity and permeability in human intestinal tissue. Jejunal tissue samples were collected from patients undergoing laparoscopic Roux-en-Y gastric bypass. Patients had given full informed consent. The study has been reviewed and approved by a regional ethical review board. Tissue samples were immediately transferred into a vessel containing cold, oxygenated Krebs-Ringer buffer and quickly transported to the laboratory. Arriving, the epithelium was dissected away from sub-epithelial tissues and mounted in horizontal as well as vertically oriented Ussing chambers with 9 mm openings between the two chambers. The basolateral chamber was filled with glucose containing Krebs-Ringer buffer, while the glucose in the apical chamber was substituted with mannitol. This is to avoid SGLT-induced tight junction opening. The chambers were kept at 37° C. and bubbled with 95% $O_2$/5% $CO_2$ for the duration of the experiment. Electrophysiology of the tissue was monitored throughout the experiment to assure continued tissue viability. After mounting, the tissues were allowed to equilibrate for 40 minutes with two medium exchange. Nanoparticles were then added to the chambers. Samples from donor and acceptor side chambers were taken at regular intervals for the 120 min duration of the experiment. At the end of the experiment, continued viability of the tissues was tested by addition of the cAMP-agonist forskolin. Viable tissue with oxidative metabolism will form cAMP in response to forskolin leading to an opening of CFTR Cl channels, the response was monitored as changes in potential difference and short-circuit current over the epithelium. The permeability of fluorescently labeled nanoparticles was analyzed in a plate reader and the apparent permeability rate constant (Papp) was calculated.

EXAMPLE 2

As indicated in the introduction, one objective of these examples was to illustrate a nanocarrier intended to help peptides overcoming the biological barriers associated to the oral modality of administration. The cell penetrating peptide R8 is able to promote insulin absorption on rat ileal tissue, and the drug-R8 binding may allow for enhanced drug transport. In these examples, modified R8 was used to from nano-size complexes with insulin, and PEGylated polymer was used to improve their stability in an enzyme rich GIT environment, as well as to optimize their interaction with the biological barriers.

Figure 1C:
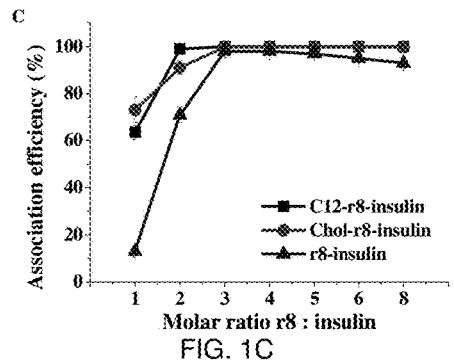
Figure 1D:
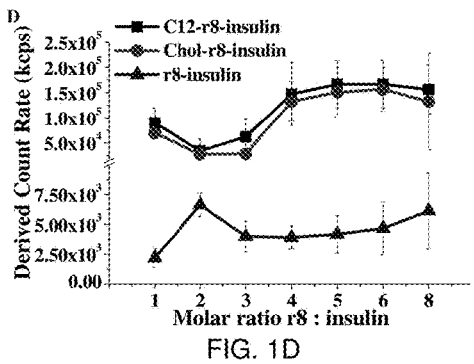

Development and physicochemical characterization of NCPs. For NCPS, two different hydrophobic derivatives of R8 were used in these examples: Cholesterol-R8 and stearic acid-R8. The influence of the pH of the insulin solution and also the R8:insulin molar ratio were analyzed. As for the influence of insulin solution pH, a pH of 11.8 (0.01 N NaOH) was observed as leading to the highest insulin association. This may be due to the fact that insulin was highly negatively charge and, thus, its interaction with R8 was maximized. On the other hand, as shown in FIG. 1, the R8:insulin molar ratio had a significant influence on the size, and zeta potential of the NCPs. The tendency observed was quite the same for the NCPs, irrespective of the hydrophobic tail associated to R8. However, the particle size and dCR (indicator of the particles concentration) was different depending on whether or not R8 was modified hydrophobically. At a molar ratio of 1:1, nanoparticles with a surface charge of −23.5 mV and −25 mV were obtained for C12-R8-insulin and Chol-R8-insulin NCPs, indicating that the insulin amount was in excess (FIG. 1A). Indeed, the association efficiency (AE) of insulin was in the range of 60-70%, being particularly low (10%) for non-modified R8-insulin complexes (FIG. 1C). In addition, the low dCR associated to these formulations, notably for the non-modified R8-insulin complexes, suggested the low yield in the complex process, having a low number of nanoparticles (as demonstrate the low dCR) (FIG. 1D). By raising the R8:insulin molar ratio, the Z-potential increased gradually along with the particle size and the AE, implying that more insulin has been associated to R8. When Z-potential of the complexes reached 0 mV (molar ratio between 2:1 to 3:1 for modified R8 and between 3:1 to 4:1 for non-modified R8), almost all the anionic insulin was complexed with the cationic phase, which led to an AE of insulin close to 100%. However, due to the lack of electrostatic repulsion between the particles, all of the complexes aggregated, displaying a particle size over a micron. Subsequently, after surpassing the barrier of modified R8:insulin molar ratio 4:1, the positive surface charge of the complexes was strong enough to prevent aggregation and, thus, to maintain the nanometric size, while the insulin AE remained 100%. After this specific ratio, the further addition of non-modified R8 did not give rise to nano-size complexes. This plateau would suggest that the saturation of the system has been achieved.

FIG. 1 shows (FIG. 1A) Z-potential, (FIG. 1B) particle size, (FIG. 1C), association efficiency, and (FIG. 1D) derived count rate of non-coated C12-R8-insulin, Chol-R8-insulin complexes and R8-insulin controls at an R8:insulin molar ratio from 1:1 to 8:1. Data is expressed as mean+/−SD, n=3.

Overall, these show that stable nanometric complexes can be obtained between hydrophobically modified insulin and R8; however the same kind of complexes could not be formed using regular R8. This suggests that the ionic interaction is not the only driving force for complex formation and the hydrophobic interactions between the C12 chain or Chol and insulin also plays a significant role. These results underline the potential advantages of the nanocomplexes vs. the regular R8-insulin complexes. The physicochemical characteristics, AE and drug loading are shown in Table 2.

A Table 2 shows physicochemical properties, AE and drug loading of non-coated C12-R8-insulin and Chol-R8-insulin NCPs at an optimum R8:insulin molar ratio. Data is expressed as mean+/−SD, n>10 for C12-R8-insulin NCPs; n=3 for Chol-R8-insulin NCPs.

TABLE 2

| Formulation | Size (nm) | PdI | Z-pot (mV) | AE (%) | Final loading (%) |
| --- | --- | --- | --- | --- | --- |
| C12-R8-insulin 8:1 | 176 +/− 16 | 0.1 | +20 +/− 1 | 100% | 33.3 |

TABLE 2-continued

| Formulation | Size (nm) | PdI | Z-pot (mV) | AE (%) | Final loading (%) |
| --- | --- | --- | --- | --- | --- |
| Chol-R8-insulin 5:1 | 171 +/− 26 | 0.1 | +29 +/− 4 | 100% | 40.8 |
| Chol-R8-insulin 6:1 | 170 +/− 24 | 0.1 | +30 +/− 3 | 100% | 36.5 |

EXAMPLE 3

Development and physicochemical characterization of enveloped ENCPs. This example illustrates the envelopment of NCPs with PEG derivatives in order to preserve their stability upon contact with intestinal fluids, and facilitate their diffusion across the mucus. In particular, a PEGylated polyanion such as PGA-PEG was studied. Two different polymers, either diblock of branch PGA-PEG (FIG. 2) were selected, and the enveloping methods either by simple incubation or film hydration was demonstrated. The NCPs including C12-R8-insulin were selected for this enveloping process. The results obtained with the hydration method indicated that the association efficiency was maintained when the enveloping material was the diblock PGA-PEG, however, the AE was compromised (from 100% to 15%) when using branch PGA-PEG polymer (FIG. 3). This was attributed to the different way the enveloping polymers interact with the R8-insulin core. The branched copolymer had an important negative charge attributed to the PGA (100 monomer units) and small 0.3 kDa PEG chains pending, whereas the diblock copolymer has only 10 units of PGA, linked in a diblock manner to 20 kDa long PEG chains. Thus, the branched negative polymer may have a tendency to displace insulin upon simple mixing. In contrast, the film hydration method (FIG. 4) allowed the efficient accommodation of both types of PGA-PEG onto the surface of the cationic NCPs cores without impairing the AE of insulin.

The efficiency of the enveloping process was also analyzed by measuring the Z-potential, the particle size and the insulin AE of the ENCPs (FIG. 3, Table 3). When using the film hydration method, the surface charge of the NCPs changed from positive to neutral or negative values due to the attachment of the branched or diblock PGA-PEG, respectively. However, only a slight decrease in the Z-potential was seen when the incubation method was used for both types of PGA-PEG. This could be explained by the fact that the film hydration medium allows a gradual and more effective interaction of the PGA-PEG molecules with the nanocomplexes, without altering the association of insulin to the modified R8.

Figure 2A:
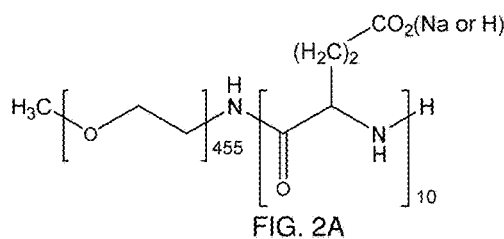
FIGS. 2A-2B illustrate the structure of certain polymers in accordance with some embodiments of the invention.
Figure 2B:
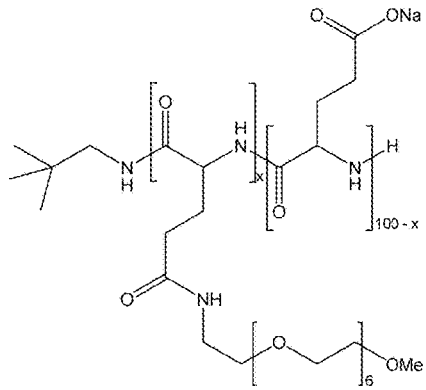

This observation was corroborated by the changes in particle size: the size decrease observed when the branched PGA-PEG was used might be attributed to the formation of a new population of nanostructures, probably due to the competitive interaction of PGA-PEG and insulin with C12-R8, which resulted in the detachment of insulin from the NCP (FIG. 2A). In contrast, the film hydration method facilitated the enveloping process, but did not influence the association of insulin in the C12-R8 molecules even using branch PGA-PEG polymer. This is possibly due to that ionic . . . teraction between the branch PGA-PEG and the NCP takes place in a slower rate when film hydration method is applied.

FIGS. 3A-3C show peptide association efficiency, Z-potential, and particle size of the non-enveloped C12-R8-insulin NCPs and those ENCPs coated by branch and diblock PGA-PEG polymers with different methods. Data is expressed as mean+/−SD, n>10 for diblock PGA-PEG ENCPs, and n=3 for the rest.

Table 3 shows physicochemical properties, AE and drug loading of C12-R8-insulin and Chol-R8-insulin ENCPs enveloped by diblock or branch PGA-PEG polymers. Data is expressed as mean+/−SD, n>10 for diblock coated C12-R8-insulin ENCPs, and n=3 for the rest.

FIG. 4 shows preparation of non-coated NCPs by hydrophobic ionic interaction and the subsequent formation of PGA-PEG enveloped ENCPs by film hydration method.

TABLE 3

| PGA-PEG, modified R8 type & R8:insulin molar ratio | Size (nm) | PdI | Z-pot (mV) | AE (%) | Final loading (%) |
|---|---|---|---|---|---|
| Branch, C12-R8, 8:1 | 220 +/− 19 | 0.1 | −44 +/− 1 | 91 +/− 6 | 18.2 +/− 1.2 |
| Diblock, C12-R8, 8:1 | 236 +/− 27 | 0.1 | +2 +/− 2 | >99 | >25.7 |
| Branch, Chol-R8, 5:1 | 202 +/− 28 | 0.2 | −43 +/− 1 | 81 +/− 4 | 18.2 +/− 0.9 |
| Diblock, Chol-R8, 6:1 | 225 +/− 10 | 0.2 | +2 +/− 3 | 92 +/− 9 | 26.8 +/− 2.6 |

As a way to corroborate that the enveloping process did not alter the particle size and morphology of the particles, both NCPs and ENCPs were observed by TEM. The size and appearance of the nanocomplexes with envelopes or not were very similar, which was consistent with the data obtained by DLS. Finally, to further assess the efficiency of the enveloping process, the stability of the ENCPs was evaluated as discussed below.

EXAMPLE 4

Improved stability of ENCPs in simulated intestinal media. The colloidal stability of the ENCPs was tested in simulated intestinal media in this example. Apart from particle size, dCR was used as an indicator of the particle concentration as a function of the time. As noted previously, the non-coated NCPs aggregated (to ~1 micrometer) immediately in SIF with a growing particle size until several microns. Once coated with either the diblock or branch PGA-PEG, the colloidal stability in SIF was greatly improved for at least 4 h (FIG. 5). The diblock PGA-PEG enveloped ENCPs exhibited more advanced stability during longer time, and thus were selected to be tested in more complex intestinal media. When incubated in FaSSIF-V2 medium, the diblock PGA-PEG enveloped ENCPs remained colloidally stable for at least 6 hours (FIG. 6). The preservation of the mean particle size and polydispersity of the population (always below 0.2) as well as the dCR indicated that no particle aggregation or degradation occurred thanks to the protection provided by PEG. Based on these data, the diblock PGA-PEG enveloped C12-R8-insulin ENCPs was used for subsequent experiments.

Figure 5A:
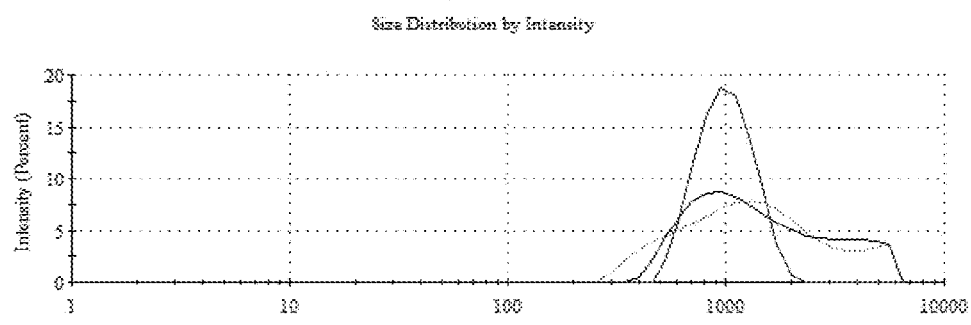
FIGS. 5A-5C illustrate sizes of particles in accordance with some embodiments of the invention.
Figure 5B:
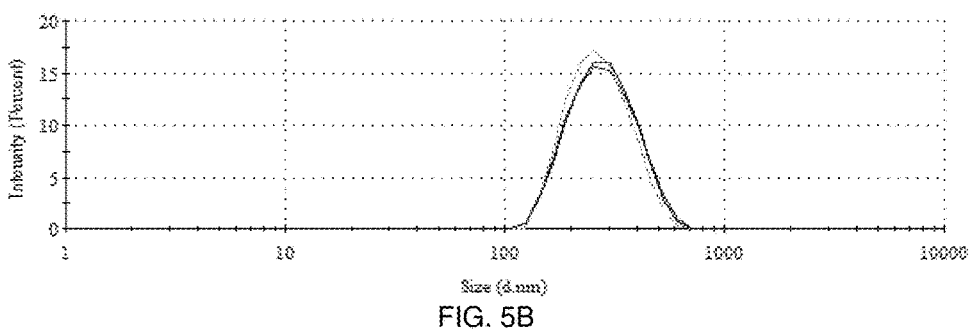
Figure 5C:
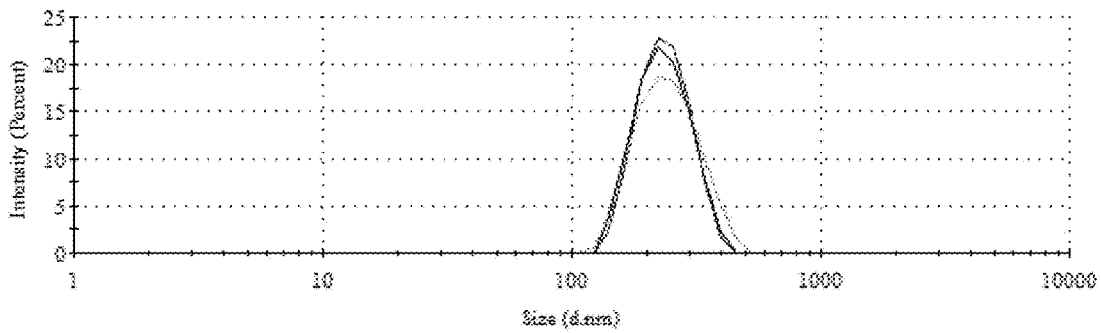

FIG. 5 shows particle size of (FIG. 5A) non-enveloped C12-R8-insulin NCPs in SIF at 0 hours, (FIG. 5B) branch PGA-PEG enveloped NCP in SIF at 4 hours, and (FIG. 5C) diblock PGA-PEG enveloped NCPs in SIF at 4 hours.

FIG. 6 shows the colloidal stability of diblock PGA-PEG enveloped C12-R8-insulin and Chol-R8-insulin ENCPs in SIF and FaSSIF-V2. FIG. 6A and FIG. 6B show the particle size and dCR of the ENCPs, respectively. The PdI remains below 0.2. Data are expressed as mean+/−SD, n=3.

Stability of ENCPs during storage and development of a freeze-dried formulation. The diblock PGA-PEG enveloped ENCPs, both C12-R8-insulin and Chol-R8-insulin, were stored at 4° C., room temperature (~20° C.), and on a 37° C. shaking bed for up to 60 days. Particle size and dCR were monitored over the time. The C12-R8-insulin ENCPs retained the same characteristics after 2 months storage under all the conditions, while a decrease in dCR was observed for the Chol-R8-insulin ENCPs, indicating decreased population due to a potential degradation or precipitation process. The diblock PGA-PEG enveloped C12-R8-glulisine ENCPs was selected as the optimum prototype for subsequent experiments. In addition, lyophilization assay showed that this prototype was able to be freeze dried and maintained its physicochemical properties when reconstituted after 2 months storage at room temperature in a desiccator.

In vitro release of insulin from ENCPs in simulated intestinal media. An in vitro release study of both non-enveloped C12-R8-insulin NCPs and the diblock PGA-PEG enveloped ENCPs was performed in SIF and FaSSIF-V2 media, at insulin concentration 0.17 mg/mL and 0.05 mg/mL. The tested formulations showed no release in both media for up to 6 hours (data not shown). These results suggest that the electrostatic/hydrophobic interaction between the R8-derivative and insulin in the C12-R8-insulin core facilitates the release process. Similar data were obtained when the NCPs and ENCPs were incubated in 100 mM pH 4.0 and 5.0 acetate buffers as well as pH 2.5 acidified water. This would indicate that the ionic force does not affect insulin release and, thus, that insulin was not expected to be released from the ENCPs in the intestinal medium. However, upon in vivo administration, the drug release could be triggered by sophisticated digestion mechanisms. Overall, these NCPs and ENCPs did not have significant burst drug release under intestinal conditions; however, the variation of pH, hydrophobic force and higher ionic strength along the GIT and in enterocytes may promote the release of insulin.

EXAMPLE 5

Prevention of proteolytic degradation of insulin associated to ENCPs. Successful peptide nanocarriers are supposed to protect the loaded drug from enzymatic degradation. In order to investigate the capacity of ENCPs to protect insulin against enzymatic degradation in the intestinal tract, a proteolysis study of the diblock PGA-PEG enveloped C12-R8-insulin ENCPs was performed in at 1% (w/v) pancreatin supplemented SIF media. As shown in FIG. 7, results revealed that after 15 min of incubation in the very drastic proteolysis media, plain insulin was totally degraded. In contrast, the NCPs efficiently protected the entrapped insulin from degradation insulin (75.6+/−8.8%). A significant amount of insulin (25.3+/−4.6%) was still active after 2 h incubation in the proteolytic medium. Taking into account that pancreatin is mainly present in the duodenum region and that the ENCPs are supposed to travel and be retained along the whole intestine, these results suggest that insulin may survive in the harsh intestinal ambient when is incorporated into the diblock PGA-PEG enveloped C12-R8-insulin ENCPs.

FIG. 7 shows a proteolysis study of diblock PGA-PEG enveloped C12-R8-insulin ENCPs and plain insulin solution incubated in 1% (w/v) pancreatin supplemented SIF media. Data are expressed as mean+/−SD, n=3.

EXAMPLE 6

Cytotoxicity of ENCPs on Caco-2 cells. The cytotoxicity of the NCPs, ENCPs and controls was evaluated in the Caco-2 cell monolayers, using the by MTS assay. After a 2 hour incubation period, a concentration-dependent cytotoxicity profile was observed for all the formulations tested. The results in FIG. 8 indicate that the NCPs exhibited an inherent toxicity at concentrations above 50-100 micrograms/mL, and that their toxicity became drastically reduced upon enveloping with PGA-PEG. The cytotoxicity of NCs was associated to both, the R8 moiety and the hydrophobic ligand being cholesterol-R8, the one displaying the highest cytotoxicity. In summary, the cytotoxicity of the different tested products followed the sequence: Chol-R8>C12-R8>ENCPs>diblock or branched PGA-PEG. In conclusion, these results showed the positive contribution of the enveloping process in terms of reducing the inherent toxicity of CPPs as penetration enhancers.

Figure 8:
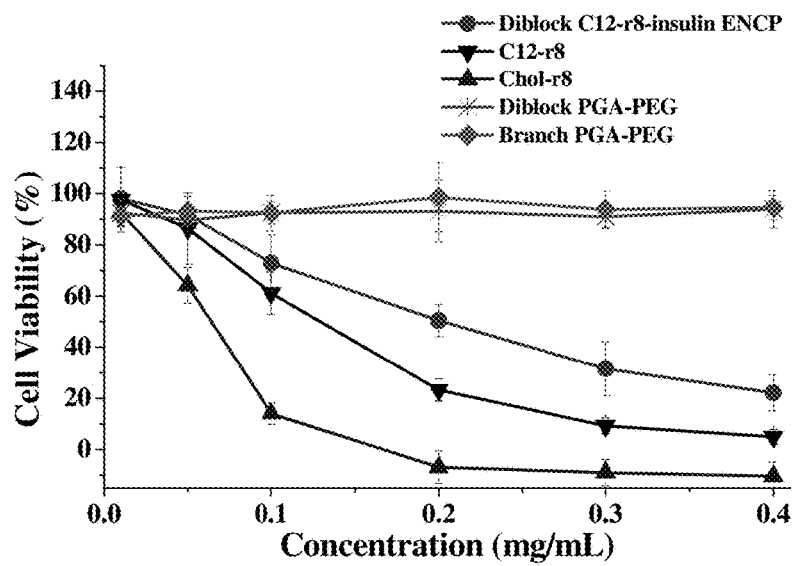
FIG. 8 illustrates cell viability, in yet another embodiment of the invention.

FIG. 8 shows cell viability of the Caco-2 cell line after 2 h incubation with diblock PGA-PEG coated C12-R8-insulin, C12-R8, Cholesterol-R8, diblock PGA-PEG copolymer and branch PGA-PEG copolymer. (Mean+/−S.D., n=9).

EXAMPLE 7

Effect of ENCPs on trans-epithelial electrical resistance (TEER) of Caco-2 cells. In this example, a study was performed to explore the capacity of ENCPs to open the intercellular tight junction for paracellular drug transport. The cells were incubated at 37° C. for 2 h with diblock or branch PGA-PEG enveloped C12-R8-insulin ENCPs as well as non-coated C12-R8-insulin NCPs at non-toxic concentration 0.01 mg/mL and 0.05 mg/mL. Simultaneously, Lucifer yellow (LY) was co-incubated with the formulations to visualize the paracellular transport effect.

The results showed that TEER values were unaffected by all types of complexes at both concentration. No significant change was found for the apparent permeability values ($P_{app}$) of LY across the Caco-2 cell monolayer (see FIG. 3), suggesting that the C12-R8 moiety was not opening tight junctions at the tested concentrations. In a second step, the TEER study was performed at 0.2 mg/mL with the 3 types of NCP and ENCPs above and physical mixture of R8 and insulin. Similar results were observed and this insignificant change in TEER indicated that the formulations were not capable to open the tight junction (see FIG. 4), excluding the possibility of paracellular transport of insulin at tested concentrations.

Quantitative cell uptake and transport of insulin associated to ENCPs. To evaluate the ability of ENCPs to transport the loaded insulin across the enterocytes, the amount of insulin internalized by the cells, and also transported across the monolayer, was quantitatively analyzed by LC/MS/MS. The enveloped ENCPs and controls (NCPs and the physical mixture of R8 and insulin) were tested at ENCP concentrations of 0.05 mg/mL and 0.2 mg/mL (the controls had the same concentration of insulin and R8). The results showed that no insulin was detected by LC-MS in the basolateral compartment or inside the cell monolayers at concentration 0.05 mg/mL (data not shown). Nevertheless, as shown in FIG. 9, at a concentration of 0.2 mg/mL, it was observed that insulin was very efficiently internalized into Caco-2 cells, when presented associated to NCPs (79.37+/−3.41%) or diblock PGA-PEG enveloped ENCPs (47.59+/−5.79%). In contrast, the internalization of insulin associated to branched PGA-PEG enveloped ENCPs was reduced (3.31+/−0.39%) and that observed for the physical mixture of R8 and insulin was negligible (0.16+/−0.04%). Even more importantly, at this concentration, a significant amount of insulin was transported to the basolateral side of the Caco-2 monolayers in the case of the diblock PGA-PEG enveloped C12-R8-insulin ENCPs (2.11+/−0.33%), whereas that associated to the branch PGA-PEG ENCPs, the non-enveloped NCPs and the physical mixture of R8 and insulin was much lower (FIG. 7).

The difference in drug uptake and cell transport efficiency could be explained on the basis of the characteristics and composition of the different nanostructures. Firstly, the differences in surface charge of the diblock PGA-PEG ENCPs (neutral), branched PGA-PEG (negative charge) and non-enveloped NCPs (positive charge) presumably played a key role in this process. Upon contact with the cells, it is believed that the NCPs with positive charge presented a stronger interaction with the cell membrane than the neutral ENCPs with a PEGylated coating. The close to zero internalization observed for the insulin associated to the branched PGA-PEG enveloped ENCPs could be due to the electrostatic repulsion between these negative carriers and negative cells membrane. On the other hand, the greater insulin transport observed for the neutral ENCPs as compared to the cationic NCPs, could be associated to the different intracellular fate of both nanocarriers.

On the other hand, the nanometric particle size of the ENCPs and NCPs may also play a role in cell uptake, a fact that justifies the drastically reduced insulin internalization into the Caco-2 monolayer when physically mixed with R8.

FIG. 9 shows apical to basolateral transportation of insulin insulin across the Transwell grown Caco-2 cell monolayer under 37° C., 2 h incubation with NCPs, ENCPs or physical mixture of R8 and insulin. n=3. The significance of differences in the mean values of different groups is evaluated using ANOVA between treatment groups followed by Tuke's multiple comparison post hoc test (SigmaPlot SyStat Software Inc., San Jose, Calif.) and data are expressed as mean+/−SD. Changes are considered statistically significant at p<0.05: *p<0.05 compared to the branch PGA-PEG coated ENCPs and R8+insulin mixture; ***p<0.05 compared to all the other groups.

In summary, these in vitro transport studies showed that the diblock PGA-PEG enveloped ENCPs were more efficient than the C12-R8-insulin NCPs for the transport of insulin across the Caco-2 monolayer, and that the physical mixture of R8-insulin was inefficient in this respect. It is believed that this performance might be further enhanced in the case of the ENCPs.

EXAMPLE 8

Figure 10A:
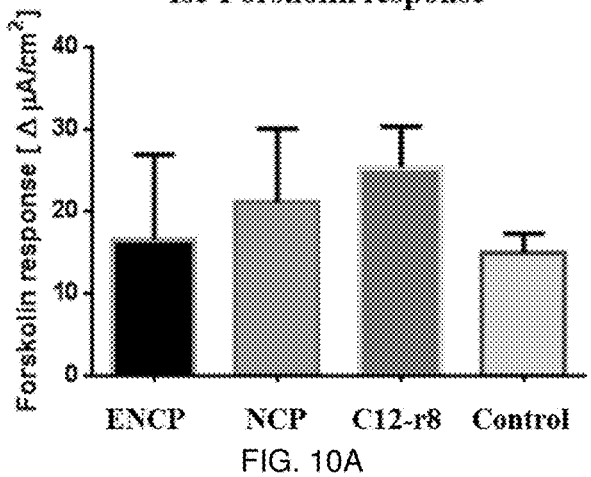
FIGS. 10A-10C illustrate forskolin response in certain embodiments of the invention.
Figure 10B:
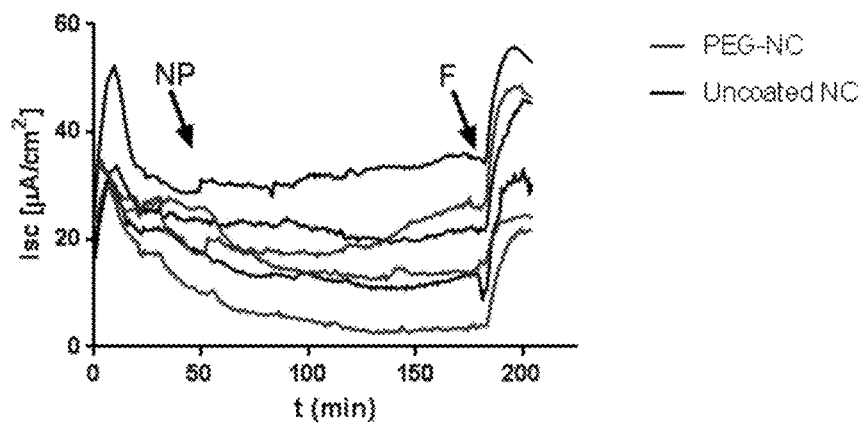
Figure 10C:
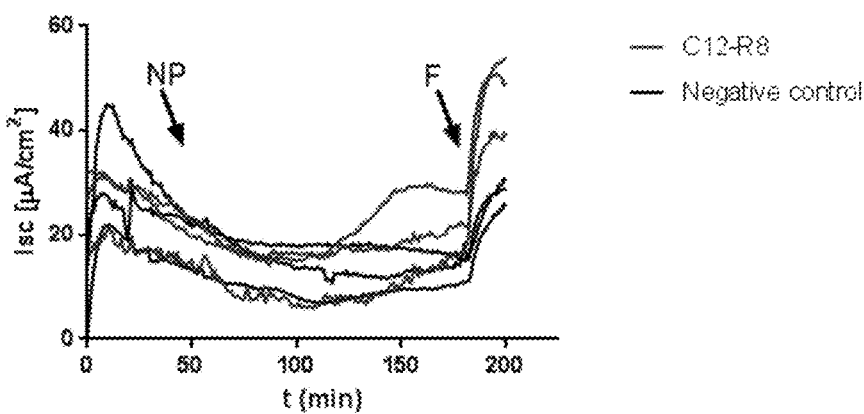

Toxicity and permeability in human intestinal tissue. In this example, in vitro cells studies showed that the neutral ENCPs effectively transported insulin across a Caco-2 mono layer. In general, the simplified and controlled conditions of the cell culture environment makes this assay a good first fast screening model. This example shows the results of the toxicity and permeability studies performed on human intestinal tissue (jejunal) mounted on an Ussing chamber. The first observation was that the addition of the ENCPs (0.2 mg/mL) onto the tissue did not cause any change in the electrophysiology parameters (FIG. 10). Concerning the toxicity profile, forskolin response was utilized as an additional control to estimate the tissue physiological function. Upon addition of this cAMP agonist, viable tissue that is able to perform oxidative metabolism will form cAMP in response, evoking increased short-circuit current (Isc). The results in FIG. 10 showed that no evident change in forskolin response was seen in the tissue incubated with either ENCPs, non-enveloped NCPs or C12-R8. Overall, considering the absence of alteration in tissue electrophysiology, it can be concluded that, under these more realistic conditions, none of the tested samples displayed any toxicity effect in human intestinal tissue.

FIG. 10 shows the forskolin response of human intestinal tissue after 3 hours of incubation with diblock PGA-PEG ENCPs, NCPs and C12-R8 compound corresponding to the same concentration as in cytotoxicity studies on Caco-2 monolayer. NP: addition of the tested samples; F: addition of forskolin. n=3.

Figure 11A:
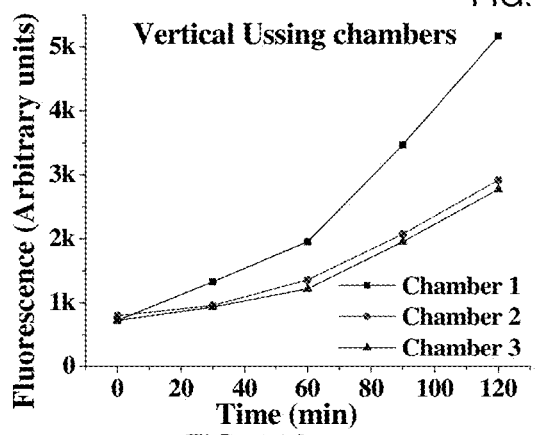
FIGS. 11A-11B illustrate transport across epithelial models in accordance with some embodiments of the invention.
Figure 11B:
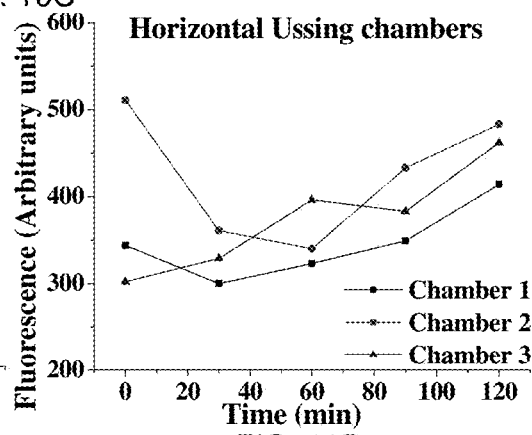

To explore the permeability of these ENCPs on human intestinal tissue, these ENCPs were labeled with the FITC fluorescent dye. The amount of ENCPs that diffused across the tissue was quantified by the fluorescence accumulation in the basolateral chamber. As shown in FIG. 11, evident particle permeation was observed in both horizontal and vertical Ussing chamber orientations. The permeation effect was more pronounced in vertical chambers, possibly due to increased contact with the tissues. By calculating the flux, 0.05-0.5% of the fluorescence associated with the ENCPs crossed the jejunal tissue in 2 h. However, no insulin amount was detectable in the basolateral receiving chamber, possibly because of the low concentration used in the study or the breaking down during the passage. The results also implied the capacity of this PEGylated prototype to diffuse across the mucus layer that covers the cells in intestinal tissue.

FIG. 11 shows apical to basolateral transport of diblock PGA-PEG ENCPs associated fluorescence across the human intestinal tissue in vertical and horizontal Ussing chambers 2 hours after exposure. n=3.

These examples illustrate a delivery carrier for oral insulin delivery. The carriers were designed taking into account of basic components: a novel penetration enhancer (hydrophobized octaarginine), and a hydrophilic envelop made of polyglutamic acid-PEG, which was intended to enhance the stability of the nanocarrier in intestinal media. The nanocarriers studied had a size around 200 nm, 100% insulin association, and a final loading up to 25.7%. In addition, the nanocarrier exhibited a number of promising biological features. The PGA-PEG enveloped the nanocarrier, making it stable in complex intestinal media containing enzymes and bile salts. This colloidal stability of the nanocarrier led, as well, to a protection of the associated insulin against degradation by enzymes. On the other hand, the presence of modified R8 led to a remarkable enhancement of insulin transport across the Caco-2 monolayer, whereas no transport was observed for a physical mixture of insulin and R8. The permeability of the nanocarriers was also validated in human intestinal tissue mounted in Ussing chambers.

EXAMPLE 9

This example shows that hydrophobically modified r8-insulin nanocomplexes are more stable from previously reported r8-insulin nanocomplexes. In this example, important differences have been identified with regard to the particle size distribution and stability between hydrophobically modified r8-insulin nanocomplexes and previously reported r8-insulin nanocomplexes. The particle size of the non-modified R8-insulin complexes was much larger than that of the modified R8-insulin complexes. Moreover, the number of particles formed (measured by the derived count rate) is much lower for the non-modified R8-insulin complexes is much larger (over 1 micrometer) than that of the modified R8-insulin complexes. Overall, this suggests that the formation process of the nanocomplexes of R8-insulin is less controlled than that of the C12-R8-insulin and Chol-R8-insulin complexes. Without wishing to be bound by any theory, this may be due to the fact that the driving force for the association between the peptide and the penetration enhancer is different. For instance, in the case of the non-modified R8-insulin complexes the association may be driven by the ionic interaction between both molecules. In contrast, hydrophobically modified R8 may have a tendency to self-assemble and interact with peptides, e.g., either through hydrophobic or ionic forces. Overall, the result is a more stable and size-controlled nanostructure due to the amphiphilic properties of the penetration enhancer.

By appearance, the suspension of the r8-insulin complex was more cloudy, and the appearance was less uniform than that of the C12-r8-insulin nanocomplex. Furthermore, the cloudiness of r8-insulin complex increased with time, while the appearance of the C12-r8-insulin suspension remained the same. After 12 hours, the r8-insulin complex precipitated on the bottom of glass vial, and the suspension media became transparent; while the C12-r8-insulin nanocomplex remained as a colloidal system with no change in appearance.

EXAMPLE 10

This example illustrates that the polyacid coating of C12-octarginine-polynucleotide may facilitate preserving the stability of the nanocomplex. This example illustrates the formation of C12-octarginine complexes with polynucleotides, using polyinosinic:polycytidylic acid (poly(I:C)) as a model polynucleotide, and their envelopment with polyglutamic acid-polyethielenglycol (PGA-PEG). This example also shows that the PGA-PEG envelop was useful for the preservation of the nanocomplex stability in biological fluids.

Nanocomplexes (NCP) between C12-r8 and poly(I:C), with a ratio 5:1 and 2:1 (w/w) were coated with PGA-PEG, obtaining a decrease in the values of the potential, which confirmed the formation of a coating. As an example, the formation of ENCPs with the 2:1 (w/w) was as follows: two mL of a C12-r8 solution (concentration of 1 mg/ml) was mixed with 1 mL of poly(I:C) (1 mg/mL). After 30 seconds of agitation and 3 minutes of stabilization, the system was characterized. For the coating with PGA-PEG, firstly 700 microliter of a solution of PGA-PEG 1 mg/mL was evaporated at 200 rpm, 37° C. for 5 minutes. Then, for the film hydration, 3 mL of NCPs were added to the flask and rotated at 200 rpm for 10 minutes, with no vacuum or temperature. Table 4 summarizes the physicochemical properties of these prototypes, both for the NCPs and the enveped nanocomplexes with PGA-PEG (ENCPs), having a C12r8:pIC ratio of 2:1 (w/w) (n=3)

TABLE 4

|  | Size (nm) | PdI | ζ-Potential (mV) |
|---|---|---|---|
| NCPs | 153 +/− 20 | 0.08 | +19 +/− 1 |
| ENCPs | 165 +/− 19 | 0.04 | +12 +/− 1 |

In order to confirm that poly(I:C) was associated, an agarose gel assay was performed. The results in FIG. 13 indicate that all poly(I:C) was associated to the ENCPs. When incubating the nanocomplexes with high amounts of heparin, a partial displacement of poly(I:C) was observed.

FIG. 13 shows an agarose gel assay on poly(I:C) association to ENCPs: Lane 1 is a DNA Ladder; Lanes 2 and 6 are ENCPs; Lanes 3 and 7 are supernatant of ENCPs; Lanes 4 and 8 are pellets of ENCPs; Lane 5 is Poly(I:C) at 4 micrograms; and Lanes 9 and 10 are ENCPs incubated with heparin for 2 h, 37° C. (mass ratio pIC/heparin 1/20)

The stability of both NCPs and ENCPs was studied in simulated intestinal media (SIF). For this assay, nanocomplexes were diluted in SIF two times and their physicochemical properties were monitored. The results in FIGS. 14A and 14B show the size and count rate of ENCPs were preserved for at least 4 hours of incubation in SIF at 37° C.

FIG. 14A shows the values of size and PdI over time, and FIG. 14B the mean count rate values.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition, comprising:
a particle comprising an inner portion surrounded by a coating, wherein the inner portion comprises a complex of a negatively charged moiety, and a positively charged peptide comprising at least 3 consecutive arginine residues linked to a hydrophobic portion, and wherein the coating comprises hyaluronic acid.

2. The composition of claim 1, wherein the negatively charged moiety comprises a peptide.

3. The composition of claim 1, wherein the negatively charged moiety comprises insulin.

4. The composition of claim 1, wherein the negatively charged moiety comprises a polynucleotide.

5. The composition of claim 1, wherein the negatively charged moiety comprises DNA.

6. The composition of claim 1, wherein the negatively charged moiety comprises RNA.

7. The composition of claim 1, wherein the negatively charged moiety comprises a protein.

8. The composition of claim 1, wherein the negatively charged moiety comprises an antibody.

9. The composition of claim 1, wherein the coating is substantially free of the positively charged peptide.

10. The composition of claim 1, wherein the coating is covalently linked to a targeting ligand.

11. The composition of claim 1, wherein the positively charged peptide comprises at least 8 consecutive arginine residues.

12. The composition of claim 1, wherein the positively charged peptide consists of RRRRRRRR.

13. The composition of claim 1, wherein the hydrophobic moiety is covalently bonded to the positively charged peptide.

14. The composition of claim 1 wherein the hydrophobic portion comprises cholesterol.

15. The composition of claim 1, wherein the hydrophobic portion comprises lauric acid.

16. The composition of claim 1, wherein the particles have an average size of less than 200 nm.

17. A composition, comprising:
a particle comprising an inner portion surrounded by a coating, wherein the inner portion comprises a complex of a negatively charged moiety, and a positively charged peptide comprising at least 3 consecutive arginine residues linked to a hydrophobic portion, and wherein the coating comprises a pegylated polyacid.

18. The composition of claim 17, wherein the negatively charged moiety comprises a polynucleotide.

19. The composition of claim 17, wherein the negatively charged moiety comprises a peptide.

20. The composition of claim 17, wherein the negatively charged moiety comprises a protein.

21. The composition of claim 17, wherein the hydrophobic moiety is covalently bonded to the positively charged peptide.

* * * * *